United States Patent
Shinde et al.

(10) Patent No.: US 10,730,986 B2
(45) Date of Patent: Aug. 4, 2020

(54) MOLECULARLY IMPRINTED POLYMERS

(71) Applicants: Sudhirkumar Shinde, Malmö (SE); Anette Gjörloff Wingren, Södra Sandby (SE); Knut Rurack, Berlin (DE); Börje Sellergren, Helsingborg (SE); Wei Wan, Berlin (DE)

(72) Inventors: Sudhirkumar Shinde, Malmö (SE); Anette Gjörloff Wingren, Södra Sandby (SE); Knut Rurack, Berlin (DE); Börje Sellergren, Helsingborg (SE); Wei Wan, Berlin (DE)

(73) Assignees: Phase Holographic Imaging PHI AB, Lund (SE); Bundesrepublik Deutschland, vertreten durch den Bundesminister für Wirtschaft und Energie, Berlin (DE)

( * ) Notice: Subject to any disclaimer, the term of this patent is extended or adjusted under 35 U.S.C. 154(b) by 152 days.

(21) Appl. No.: 15/572,962

(22) PCT Filed: May 9, 2016

(86) PCT No.: PCT/SE2016/050413
§ 371 (c)(1),
(2) Date: Nov. 9, 2017

(87) PCT Pub. No.: WO2016/182494
PCT Pub. Date: Nov. 17, 2016

(65) Prior Publication Data
US 2018/0142053 A1     May 24, 2018

(30) Foreign Application Priority Data

May 9, 2015 (SE) ..................... 1530062

(51) Int. Cl.
| | | |
|---|---|---|
| C08F 251/00 | (2006.01) | |
| A61K 47/36 | (2006.01) | |
| A61K 31/726 | (2006.01) | |
| B01D 15/38 | (2006.01) | |
| B01J 20/26 | (2006.01) | |
| B01J 20/285 | (2006.01) | |
| C08F 292/00 | (2006.01) | |
| B01J 20/30 | (2006.01) | |
| C08F 220/00 | (2006.01) | |

(52) U.S. Cl.
CPC .......... C08F 251/00 (2013.01); A61K 31/726 (2013.01); A61K 47/36 (2013.01); B01D 15/3852 (2013.01); B01J 20/261 (2013.01); B01J 20/267 (2013.01); B01J 20/268 (2013.01); B01J 20/285 (2013.01); B01J 20/3071 (2013.01); B01J 20/3085 (2013.01); C08F 292/00 (2013.01); C08F 220/00 (2013.01); C08F 2438/03 (2013.01)

(58) Field of Classification Search
CPC ..... C08F 251/00; A61K 47/36; A61K 31/726; B01J 20/268; B01J 20/285; B01D 15/3852
See application file for complete search history.

(56) References Cited

PUBLICATIONS

Kugimiya et al., Biosensors and Bioelectronics, Mar. 2001, vol. 16, pp. 1059-1062.*
Akimitsu Kugimiya, et al. "Surface plasmon resonance sensor using molecularly imprinted polymer for detection of sialic acid", Biosensors and Bioelectronics, vol. 16, No. 9-12, Dec. 1, 2001 (Dec. 1, 2001), pp. 1059-1062.
S. A. Piletsky, et al. "A Biomimetic Receptor System for Sialic Acid Based on Molecular Imprinting", Analytical Letters, vol. 29, No. 2, Jan. 1, 1996 (Jan. 1, 1996), pp. 157-170.
Helen Wilcock, et al. "End group removal and modification of RAFT polymers", Polymer Chemistry, Royal Society of Chemistry, GB, vol. 1, Dec. 23, 2009 (Dec. 23, 2009), pp. 149-157.
Kasper Eersels et al. "Selective Identification of Macrophages and Cancer Cells Based on Thermal Transport through Surface-Imprinted Polymer Layers", ACS Applied Materials & Interfaces, vol. 5, No. 15, Aug. 14, 2013 (Aug. 14, 2013), pp. 7258-7267.
Lin Zian, et al. "Preparation of boronate-functionalized molecularly imprinted monolithic column with polydopamine coating for glycoprotein recognition and enrichment", Journal of Chromatography A, vol. 1319, Sep. 24, 2013 (Sep. 24, 2013), pp. 141-147.
Wei Wan, et al. "Fluorescent Sensory Microparticles that "Light-up" Consisting of a Silica Core and a Molecularly Imprinted Polymer (MIP) Shell", Angewandte Chemie International Edition, vol. 52, No. 27, Jul. 1, 2013 (Jul. 1, 2013), pp. 7023-7027.
Supplementary European Search Report dated Dec. 12, 2018 for Application No. 16793088.2-1101.

* cited by examiner

*Primary Examiner* — Robert D Harlan
(74) *Attorney, Agent, or Firm* — Moser Toboada

(57) ABSTRACT

The present invention relates to a molecularly imprinted polymer for binding glycans, wherein the molecularly imprinted polymer is obtainable by providing a saccharide template such as a glycan; providing at least two functional monomers capable of cooperatively; interacting with the template; providing a crosslinking monomer; polymerizing the monomers optionally dissolved in a solvent, in presence of the saccharide template; and removing the template from the formed polymer. The invention is also related to a method for their production and use of the molecularly imprinted polymer.

35 Claims, 25 Drawing Sheets

Figure 3A

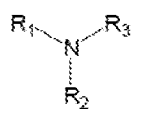 general formula for monomers containing amino groups.
At least one of $R_1$, $R_2$, $R_3$ is a polymerizable group.

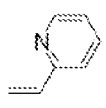 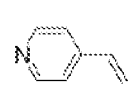 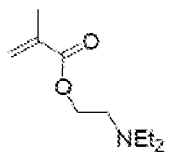 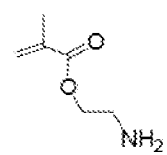 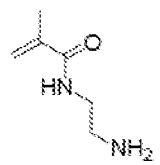

2-VPY     4-VPY     DEAEMA     AEMA     AEMAM

 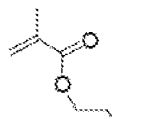  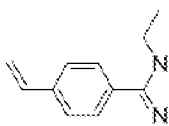 

VIM     DMAEMA     ALAM     VDEAB     VBA cationic monomers:

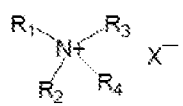 general formula for monomers containing ammonium groups.
At least one of $R_1$, $R_2$, $R_3$ and $R_4$ is a polymerizable group. $X^-$ is a counteranion.

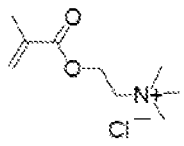 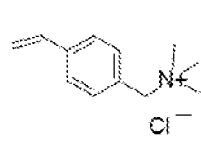 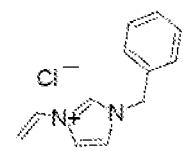 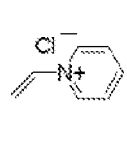

TMAEMA     TMVBA     VBI     N-VPY acidic monomers:

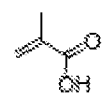 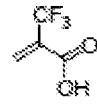 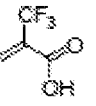 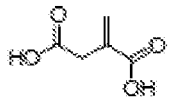 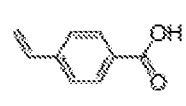 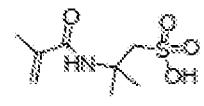

MAA     AA     TFM     ITA     PVB     AMPSA

A.

B.

C.  D.

MOLECULARLY IMPRINTED POLYMERS

TECHNICAL FIELD OF THE INVENTION

The present invention describes new molecularly imprinted polymers for binding glycans, a method for their production and use of the glycan binding polymers.

BACKGROUND ART

Cell surface glycans refer to a vast variety of glycan motifs attached to plasma membrane bound proteins or lipids. These constitute the outermost surface of the cell and are involved in cellular communication and processes like host-pathogen recognition, infection, cellular differentiation, proliferation and migration. Around 700 proteins are required to generate the full diversity of mammalian glycans, which are assembled from ten monosaccharides only: fucose (Fuc), galactose (Gal), glucose (Glc), N-acetylgalactosamine (GalNAc), N-acetylglucosamine (GlcNAc), glucuronic acid (GlcA), iduronic acid (IdoA), mannose (Man), sialic acid (SA) and xylose (Xyl). The most-widely occurring cancer-associated changes in glycosylation are sialylation, fucosylation, O-glycan truncation, and N- and O-linked glycan branching (Chart 1).

SA are the outermost monosaccharide units on the glycan chains of glycolipids and glycoproteins and often the recognition sites where the pathogens attach. The occurrence of SA has proven to correlate with several disease states such as cardiovascular, and neurological diseases as well as cancer (B. Adamczyk, T. Tharmalingam and P. M. Rudd, *Biochimica et Biophysica Acta (BBA)—General Subjects*, 2012, 1820, 1347-1353). Clinically, increased sialylation is often associated with invasiveness and poor prognosis of cancer patients. An incomplete synthesis process leads to the biosynthesis of truncated structures, as seen with STn (Chart 1) expression in gastrointestinal and breast cancers. STn (Neu5Acα2-6GalNAcα—O—R) and Tn (GalNAcα—O—R) have attracted wide spread attention as a diagnostic as well as therapeutic target since it is expressed in 80% of human cancers and absent or only weakly expressed in normal tissue. However, it has been difficult to produce IgG antibodies against Tn and ST and IgG antibodies against STn have low affinity and perform poorly in capture strategies. The few lectins available to SA (SNA and MAA) have broad specificities and low affinities, and perform poorly in capture assays.

Conversely, neo-synthesis, commonly observed in advanced stages of cancer, refers to the cancer-associated induction of certain genes involved in the expression of carbohydrate determinants, as seen in the de novo expression of certain antigens, such as sialyl Lewis a (SLea) and sialyl Lewis X, SLex, in many cancers. Polysialic acid is increased sialylation associated with several types of cancers, and frequently expressed in high-grade tumours.

There are two main mammalian SAs, Neu5Ac (N-acetylneuraminic acid) and Neu5Gc (N-glycolylneuraminic acid) (see Chart 1), which differ only by one oxygen atom and is added by the enzyme cytidine monophosphate N-acetylneuraminic acid hydroxylase (CMAH) in the cytosol. Humans lack this enzymatic activity due to an inactivating mutation of the CMAHgene. As this alternative form of SA is not normally present, immunological tolerance fails to develop. As a result, when Neu5Gc incorporation into glycoconjugates occurs after intake from dietary sources, "autoantibodies" to this sugar develop, and these have been proposed to enhance inflammatory pathways associated with cancer initiation. Novel affinity reagents for discriminating these forms as well as linkage specific animal and human glycosylations 2-3 versus 2-6 linked sialic acids are highly demanded.

Analyzing and determining these glycosylation motifs is therefore an important diagnostic goal but the task has proven challenging due to the limited availability of lectins and glycan specific antibodies (N. Fujitani, J.-i. Furukawa, K. Araki, T. Fujioka, Y. Takegawa, J. Piao, T. Nishioka, T. Tamura, T. Nikaido, M. Ito, Y. Nakamura and Y. Shinohara, *Proceedings of the National Academy of Sciences*, 2013, 110, 2105-2110).

A number of sensitive methods have nevertheless been published that either measure total sialic acid content or different sialic acid types. These methods are costly, laborious and time consuming, and commonly require sophisticated instrumentation as skilled operators for their implementation. They are therefore not well suited for routine applications. Lectin-based assays exist for a few types of sialic acids but assay development is often hampered by their low sensitivity and poor specificity. The detection of sialic acid in sialoglycoprotein or as a free moiety include the use of high performance liquid chromatography (HPLC), gas-chromatography combined with mass spectrometry (GC-MS), nuclear magnetic resonance spectrometry (NMR) and capillary electrophoresis (CE). These methods are complicated by significant requirements for sample preparation, specialised equipment, purification of the target protein and lengthy and complex data analysis for monitoring the sialylation pattern.

This warrants the development of alternative glycan specific receptors which could be used for e.g. cell or tissue imaging, cell sorting, targeted glycomics and cellular glycosylation biomarker analysis or for applications in medicine for instance for targeted drug delivery or the selective inhibition of cell surface interactions. A plethora of low molecular hosts has been systematically designed and conjugated e.g. to fluorescent reporter groups or quantum dots for imaging applications. The most powerful hosts for sialic acid feature two or more orthogonal binding groups, a boronic acid directed towards the diol functionality and a charged or neutral anion receptor directed towards the carboxylate function. Other strong binders are multi-functional incorporating two or more boronic acid groups. The latter engage in a pH dependent reversible esterification with the diols resulting in five or six membered cyclic structures.

It has long been known that monosaccharide selective receptors can be prepared by the technique of molecular imprinting. Wulff et al. reported highly discriminative boronate-based receptors for mannose, fructose and galactose prepared using the monosaccharide templates conjugated to two molecules of vinylbenzeneboronic acid (1). Other researchers later adopted this procedure for the synthesis of sialic acid imprinted bulk polymers or sensor coatings. These boronic acid containing MIPs featured strong template affinity when probed in basic buffer/acetonitrile mixtures (pH 8). A simpler one-pot protocol was subsequently used for the synthesis of glycoprotein selective MIPs (X. Bi and Z. Liu, *Analytical Chemistry*, 2013, 86, 959-966). Here the boronate monomer is conjugated in situ under base catalysis to the SA containing glycoprotein and subsequently copolymerized with a crosslinking monomer to form the imprinted polymer. The SA imprinted receptors reported so far display only weak binding for the saccharide targets ($K<10^3$ $M^{-1}$) when probed in water and especially under physiological conditions. This contrasts with the most powerful designed hosts (vide supra) where binding is sufficiently strong (>$10^5$ $M^{-1}$) to allow cell based imaging or even cell sorting applications. The latter receptors however are complicated to design for targeting more complex glycans such as disaccharide and higher saccharides. This commonly requires extensive synthetic efforts and testing of a large number of analogs in order to identify strong binders.

Apart from cell or tissue imaging applications such receptors could be used to replace lectins or antibodies in targeted glycomics, in glycan sensors, for enrichments of specific glycan motifs, for cell sorting or in medicine for instance for targeted drug delivery or the selective inhibition of cell surface interactions.

One application concerns the identification and molecular characterization of circulating tumor cells (CTCs) in cancer patients. Characterising these cells is important for understanding the metastatic process and potential therapeutic strategies thereby guiding prognosis and treatment. Progress in this field has been slow which partly is due to the low, "needle in a haystack", abundance of CTCs. Although CTCs can be reliably detected in patients with metastatic disease, challenges remain to detect early stage, treatable cancers with inferior CTC numbers. The currently dominating techniques to detect CTCs are cytometric assays where cells remain intact preceeded by an initial enrichment step to optimize the probability of rare cell detection. The dominating enrichment technique is based on immunomagnetic separation typically dependent on the epithelial protein marker (EpCam). However, cell surface glycans or circulating O-glycoproteins shed from cancer cells also represent important serum biomarkers for diagnostic and prognostic purposes. Selective detection of cancer-associated aberrant glycoforms of circulating O-glycoprotein biomarkers can increase specificity of cancer biomarker assays.

Targeted delivery of drugs to tumors represents a significant advance in cancer diagnosis and therapy. Therefore, development of novel tumor-specific ligands or pharmaceutical nanocarriers is highly desirable. These nanocarriers would be loaded with drugs and targeted to specific parts of the body where there is solely diseased tissue, thereby avoiding interaction with healthy tissue. Targeted delivery to specific cell organelles through endocytosis of the delivery vehicle (nanocarrier) offers a more specific targeting especially suited for macromolecular drugs. Selective targeting of such nanocarriers to cells expressing cancer associated glycans is an important goal.

SUMMARY OF THE INVENTION

This invention discloses glycan specific molecularly imprinted polymers (MIP) featuring moderate ($10^3$-$10^5$ $M^{-1}$) to high (>$10^8$ $M^{-1}$) affinity for a glycan wherein said MIP has been prepared using a template selected from one or more monosaccharides, disaccharides or higher saccharides comprising glycans or glycan containing molecules or species including glycoproteins, glycolipids, oligosaccharides or proteoglycans.

In one embodiment the template corresponds to the outermost terminal part of a glycan comprising one to five saccharides, commonly including sialic acid as the terminal saccharide.

In another embodiment the glycan incorporates one or more sugar acids preferably sialic acids or glucuronic acids.

In another embodiment the glycan incorporates one or more sulphate or phosphate groups.

The MIP is characterised in that it is prepared using at least one monomer, selected from a crosslinking monomer and/or a functional monomer which is polymerised in presence of the template and optionally a solvent—the template is removed from the resulting polymer, to give the molecularly imprinted polymer (MIP).

In one embodiment the MIP is prepared using at least two functional monomers containing orthogonal binding groups such as a boronic acid and/or cationic groups and/or hydrogen bonding groups.

In a second embodiment the MIP exhibits a guest responsive fluorescence incorporating a fluorescent moiety responding to binding with a change in the fluorescence.

In a third embodiment, the MIP is prepared in the form of particles having a core shell morphology, comprising an imprinted shell and a functional or non-functional core.

The receptors are moreover robust and stable with a long shelf life and can be prepared using simple procedures at low cost. These features hence circumvents the drawbacks mentioned above. The receptors are prepared using a novel imprinting approach resulting in significantly enhanced binding affinity for the glycan targets. This allows the design of glycan specific receptors for disaccharides and more complex targets comprising higher saccharides and branched structures as those found in for instance tumour specific saccharides such as the Lewis X tetrasaccharides.

In a forth embodiment, the MIPs are used in cell or tissue imaging, cell sorting, glycomics and cellular glycosylation biomarker analysis or for applications in medicine for instance for targeted drug delivery or the selective inhibition of cell surface interactions.

In a fifth embodiment, the MIPs are used for the identification and molecular characterization of circulating tumor cells (CTCs) in cancer patients.

In a sixth embodiment, the MIPs exerts a therapeutic action through endocytosis or are used therapeutically for intracellular targeted delivery of drugs through endocytsis.

BRIEF DESCRIPTION OF THE DRAWINGS

Chart 1. Examples of glycans targeted by the saccharide imprinted polymer. The template can correspond to a fragment of the glycan or the entire glycan structure.

Chart 2. Principle of imprinting a saccharide using at least two and preferably three functional monomers orthogonally binding to different subunits of the template. Chart 2 discloses examples of glycans targeted by the saccharide imprinted polymer. The template can correspond to a fragment of the glycan or the entire glycan structure.

Figure 1:
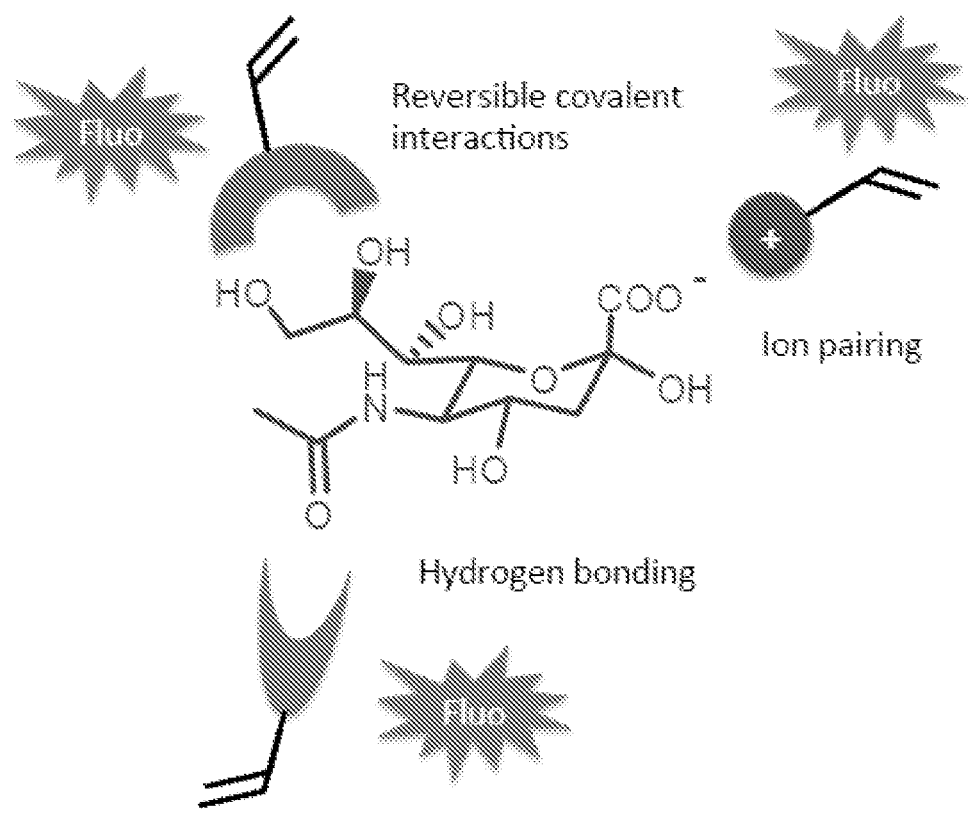
Figure 2:
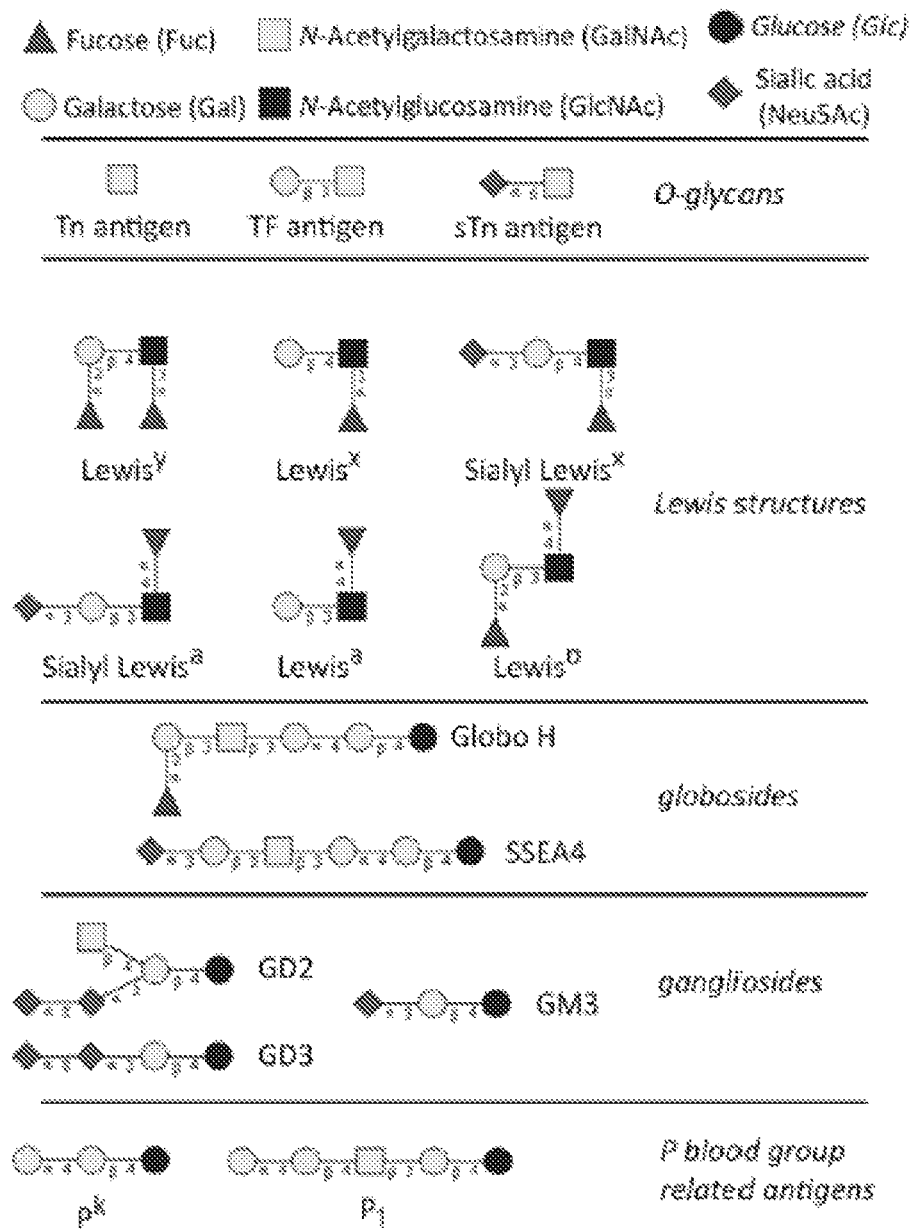
Figure 3B:
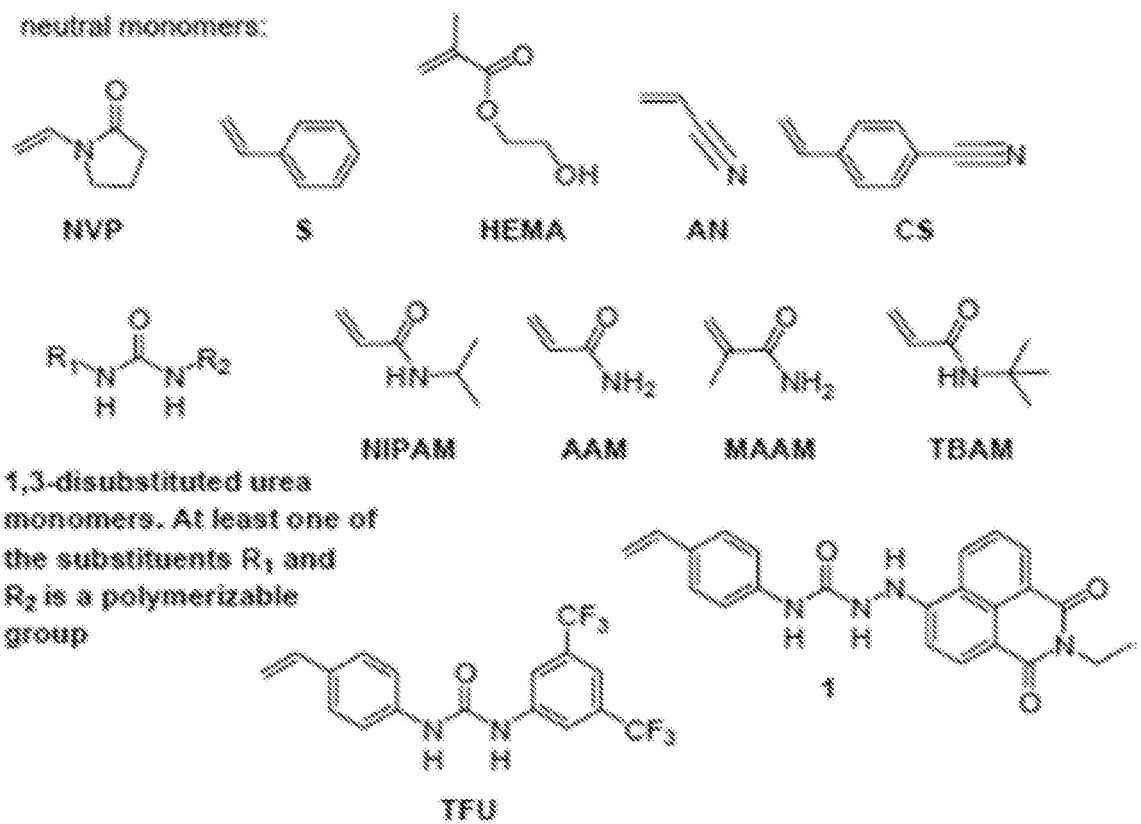
Figure 3C:
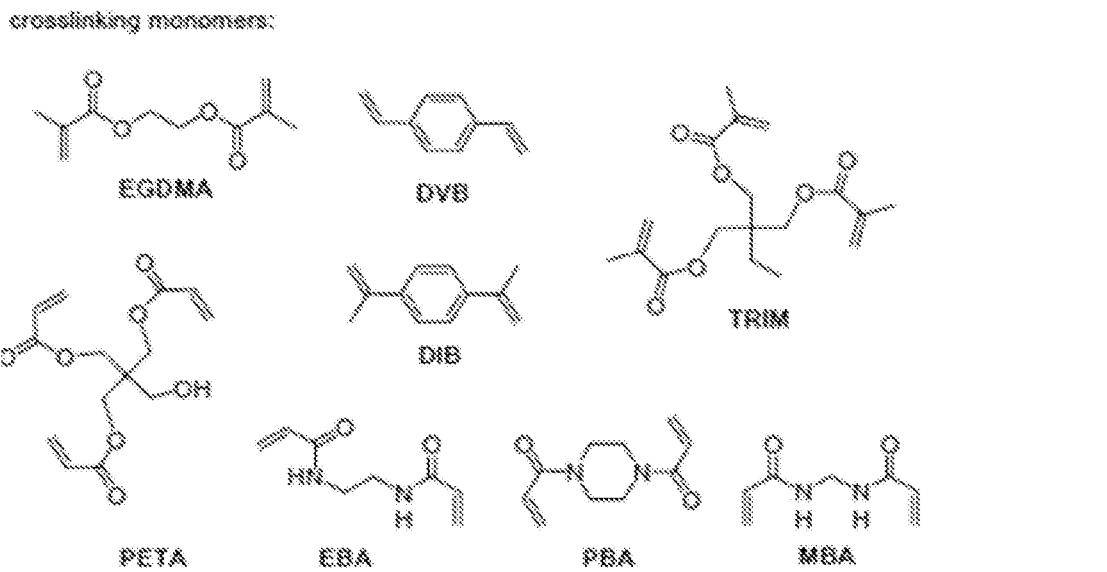
Figure 3D:
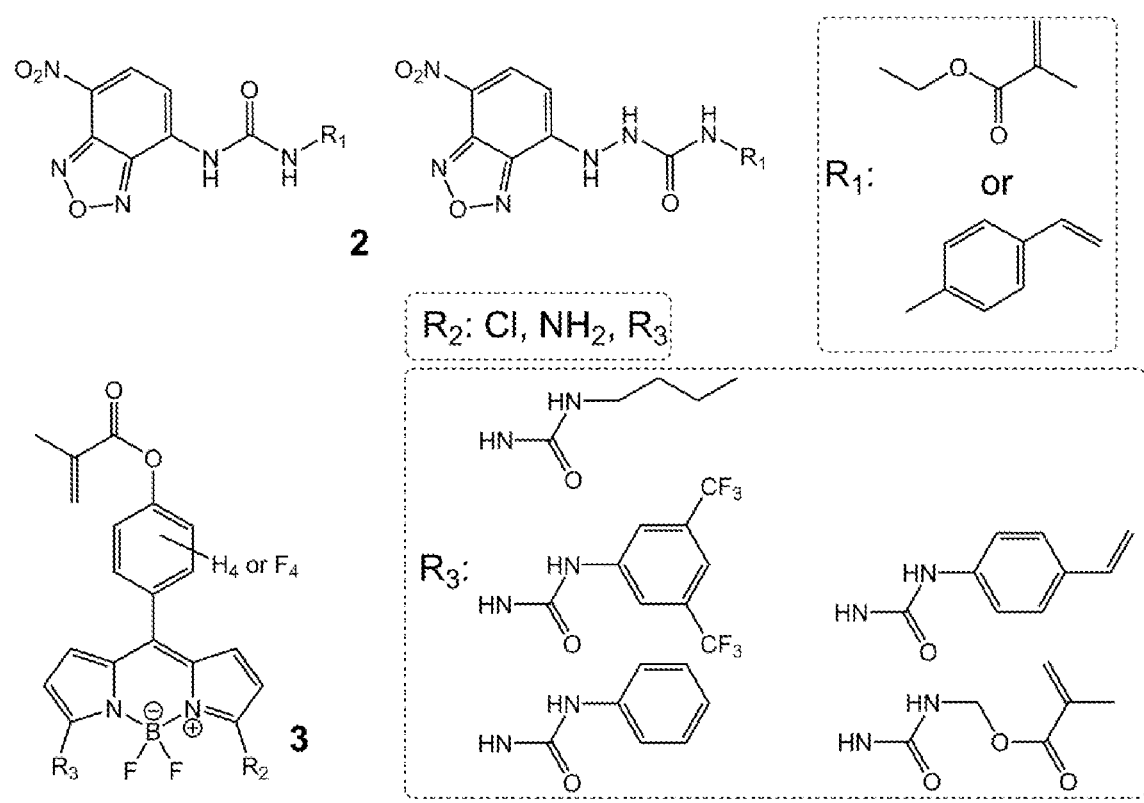
Figure 3E:
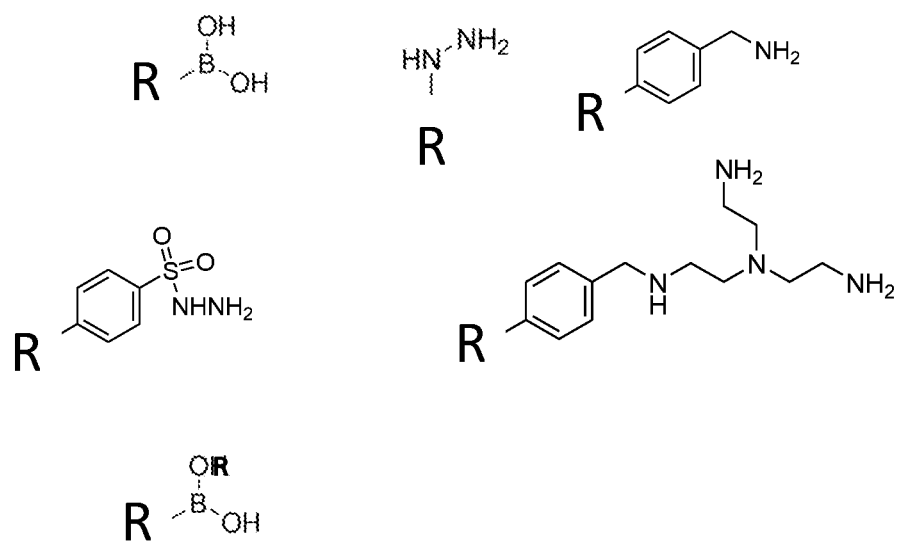
Figure 3F:
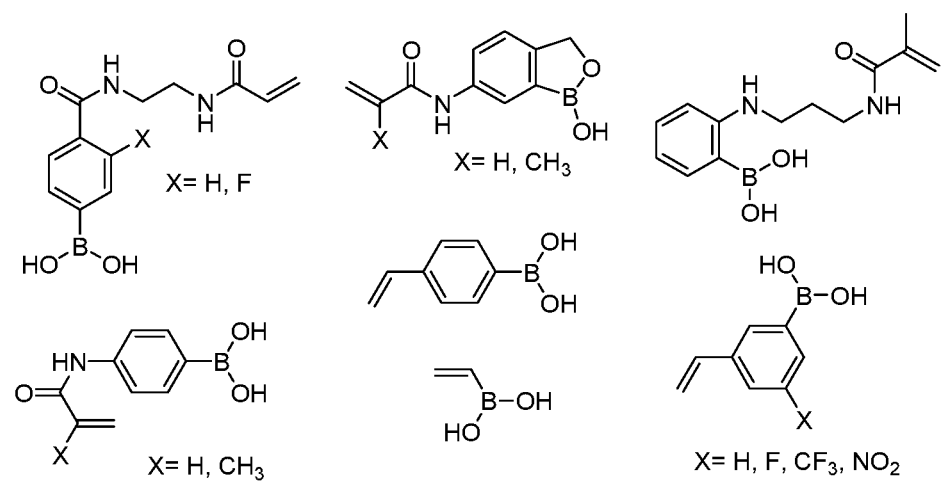
Figure 4:
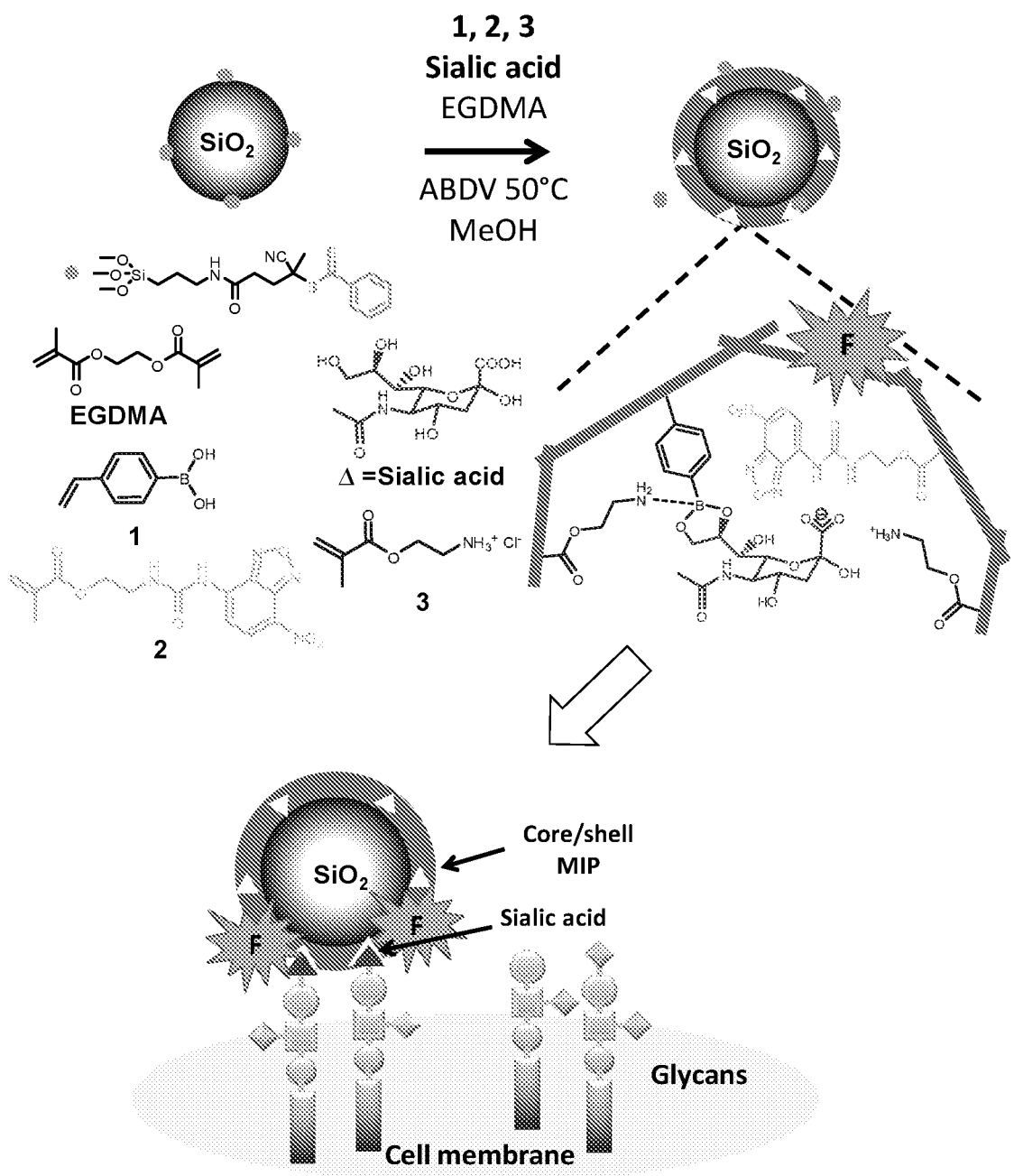
Figure 5:
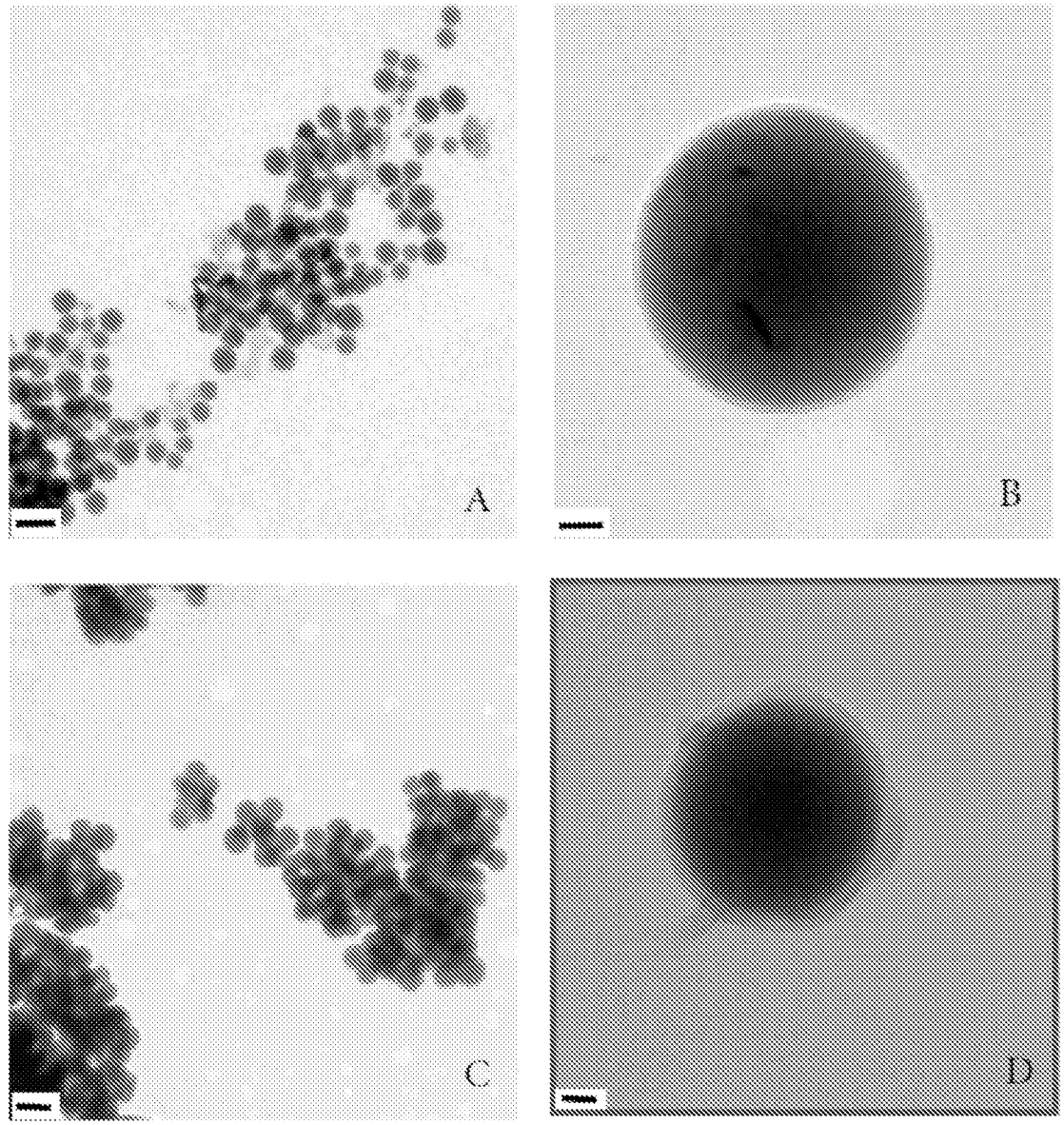
Figure 6:
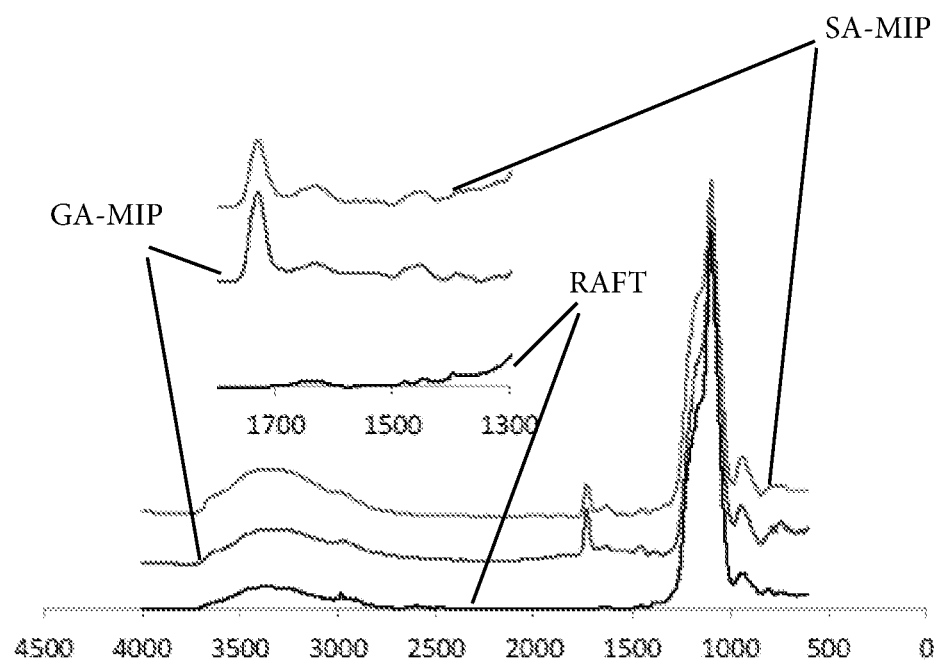
Figure 7:
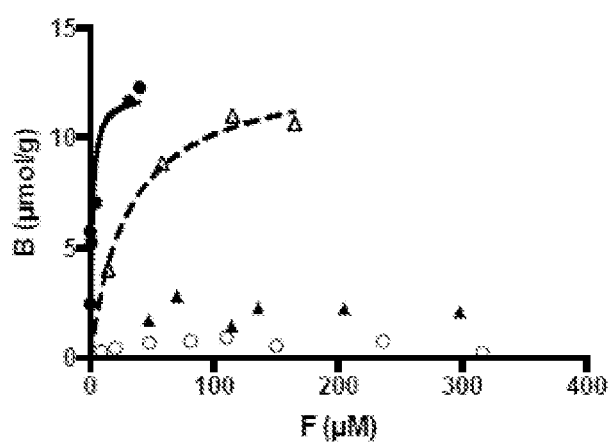
Figure 7:
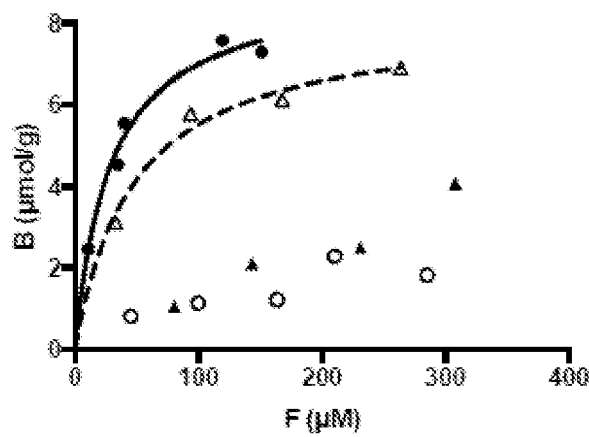
Figure 7:
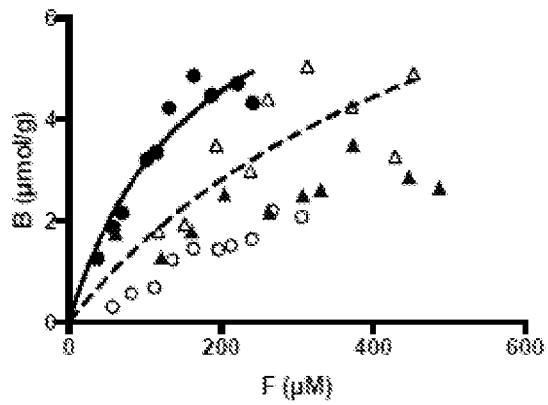
Figure 8:
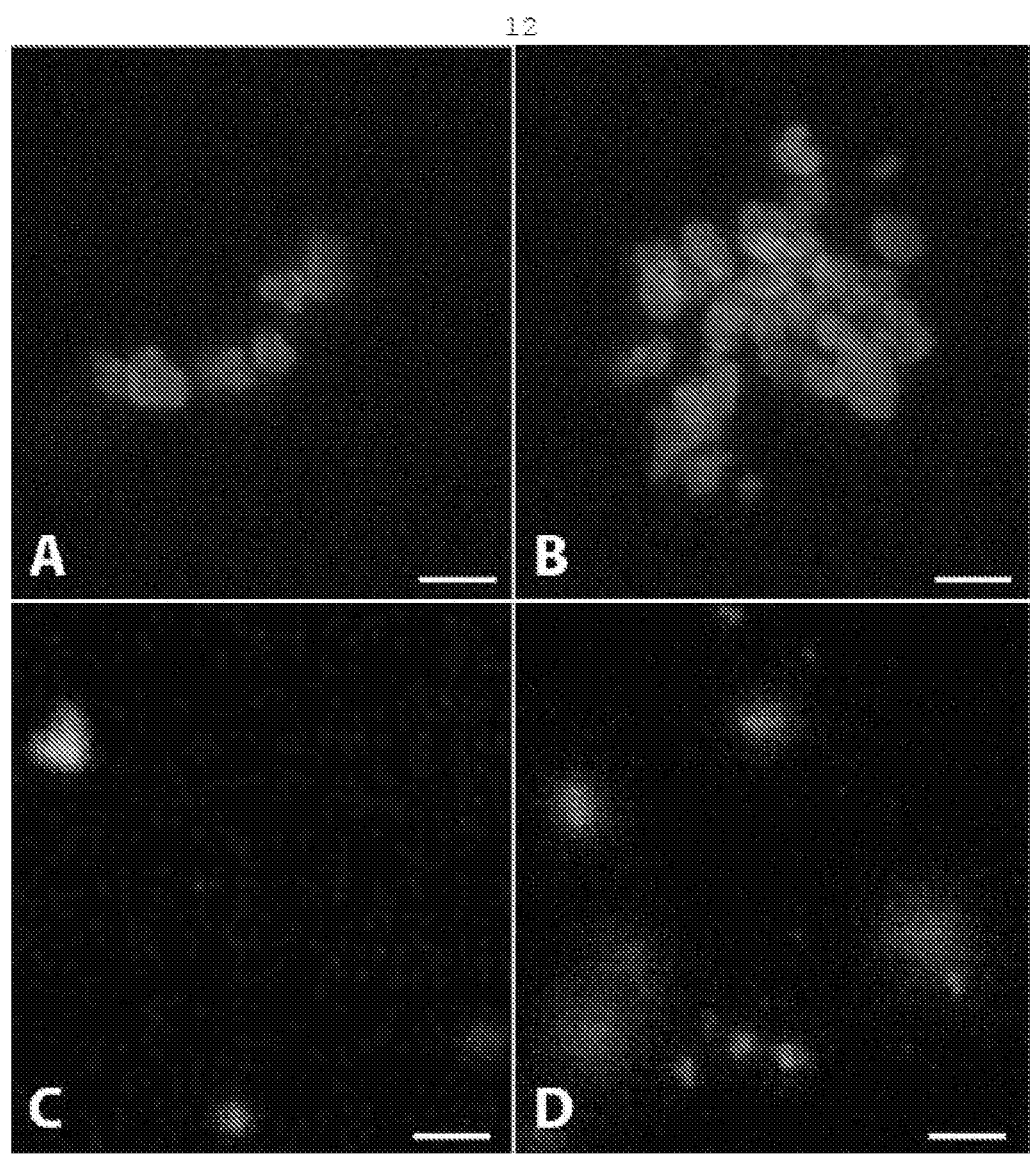
Figure 9:
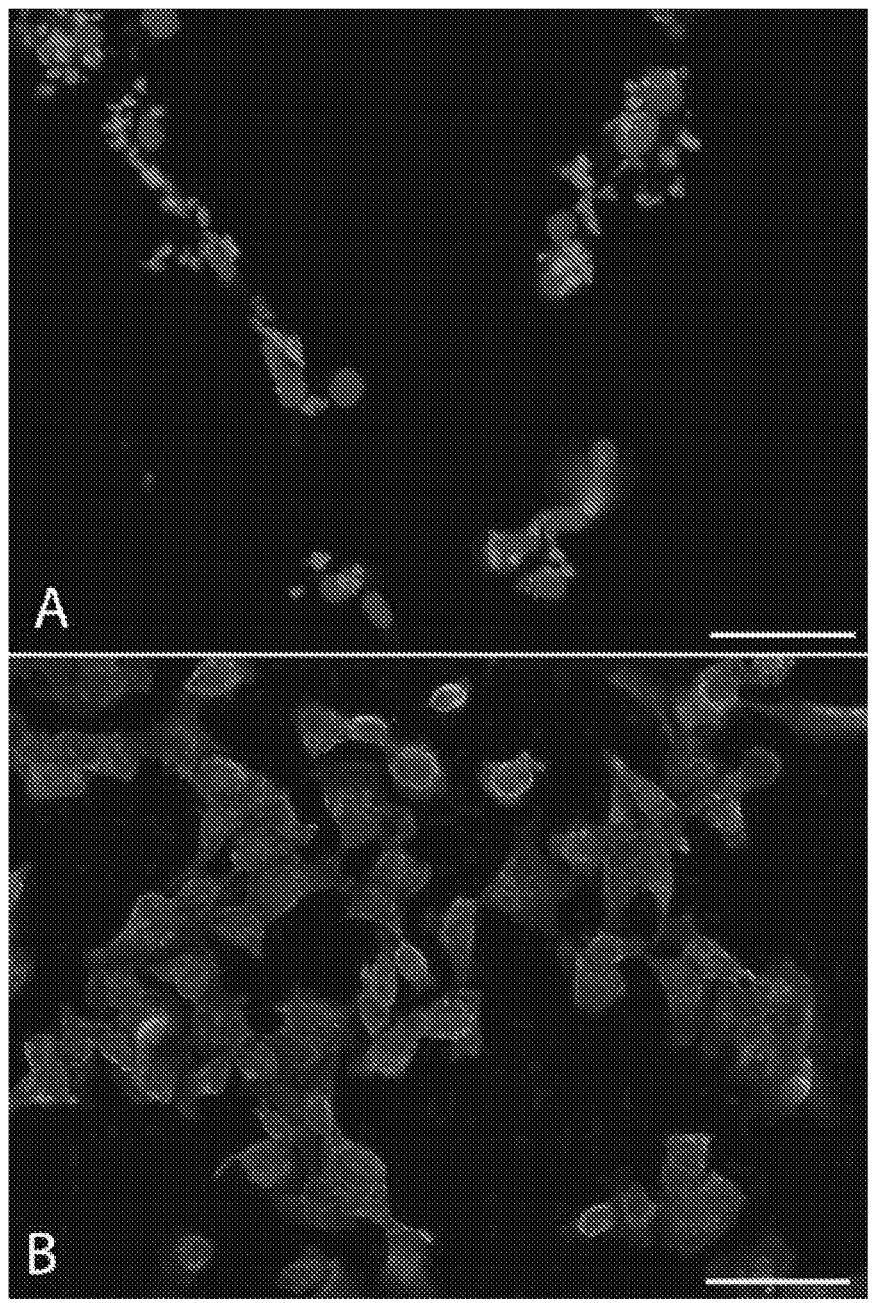
Figure 10:
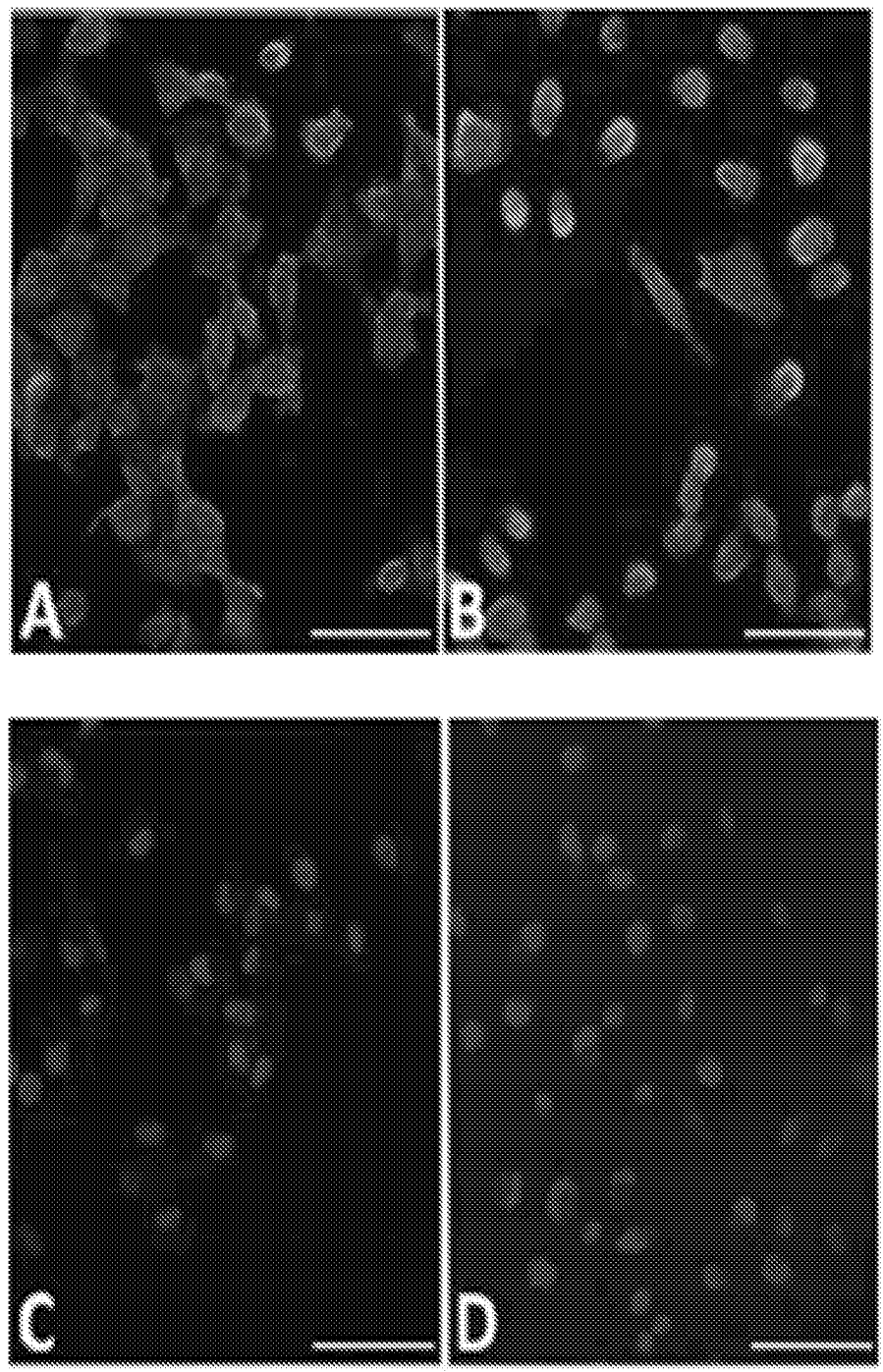
Figure 11:
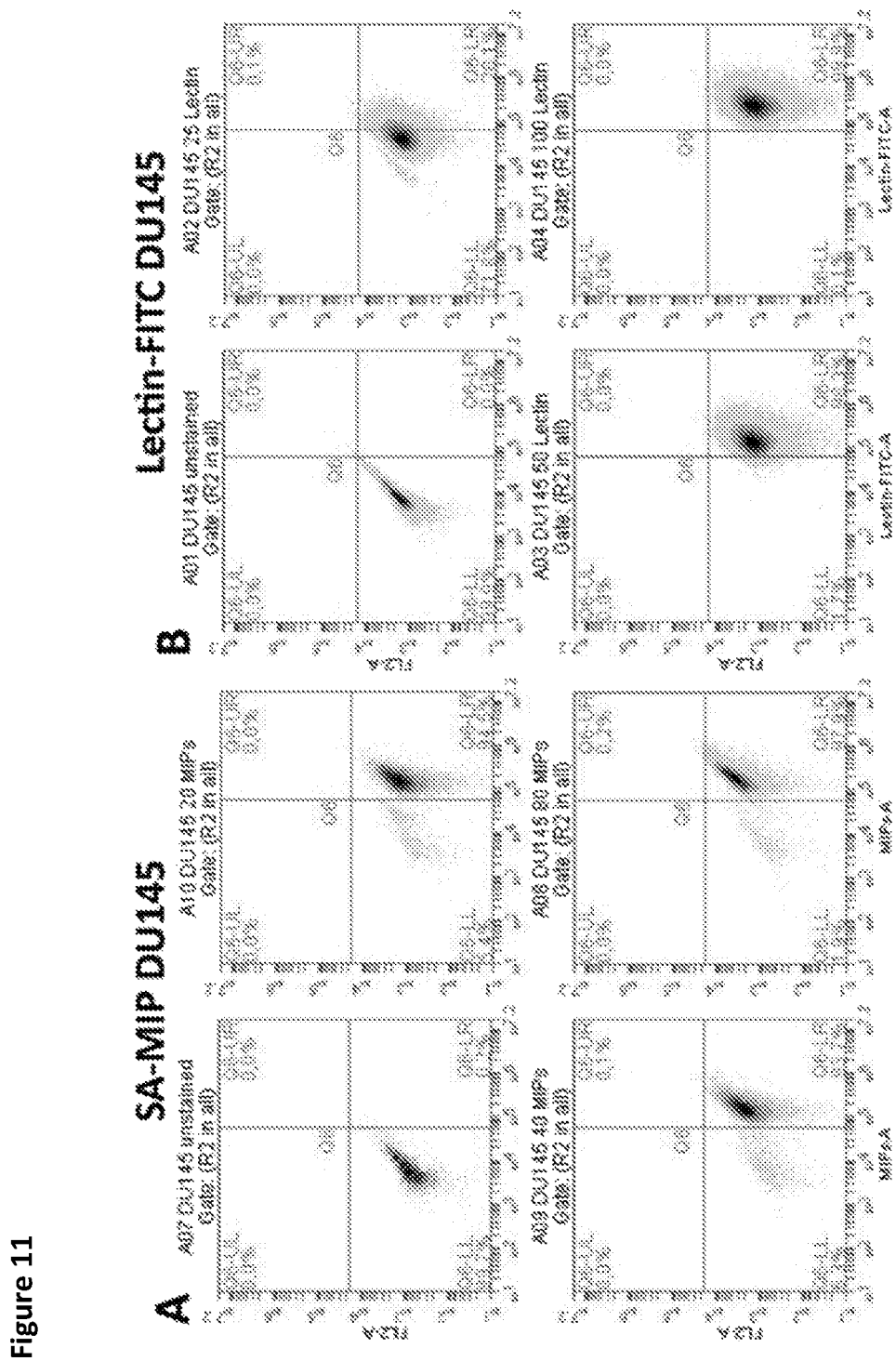
Figure 12:
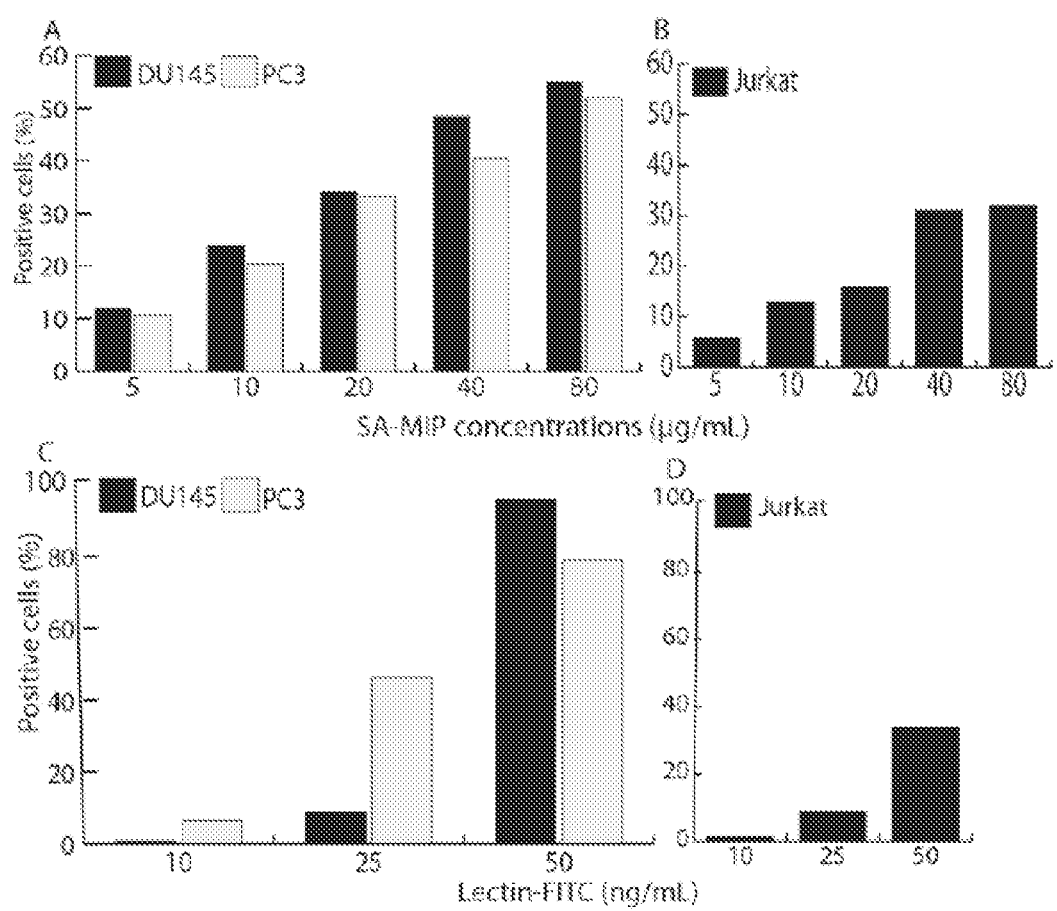
Figure 13:
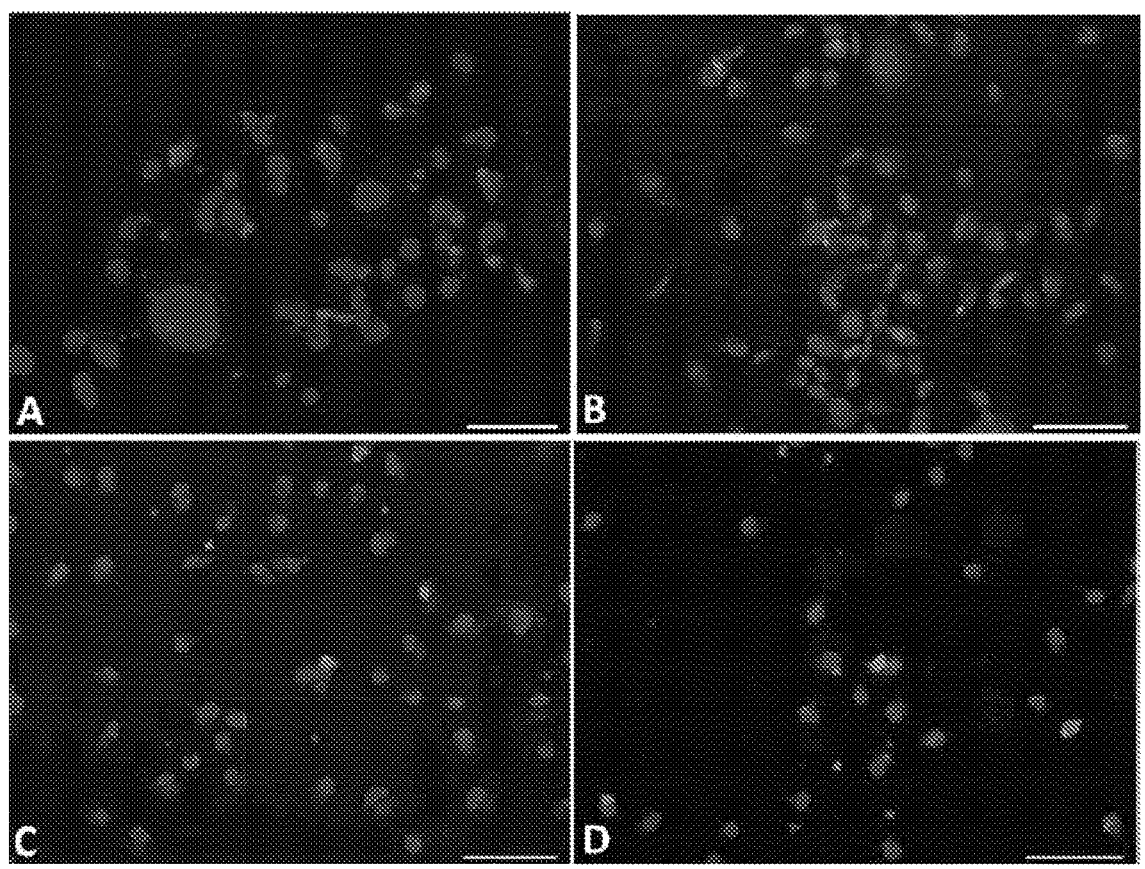
Figure 14:
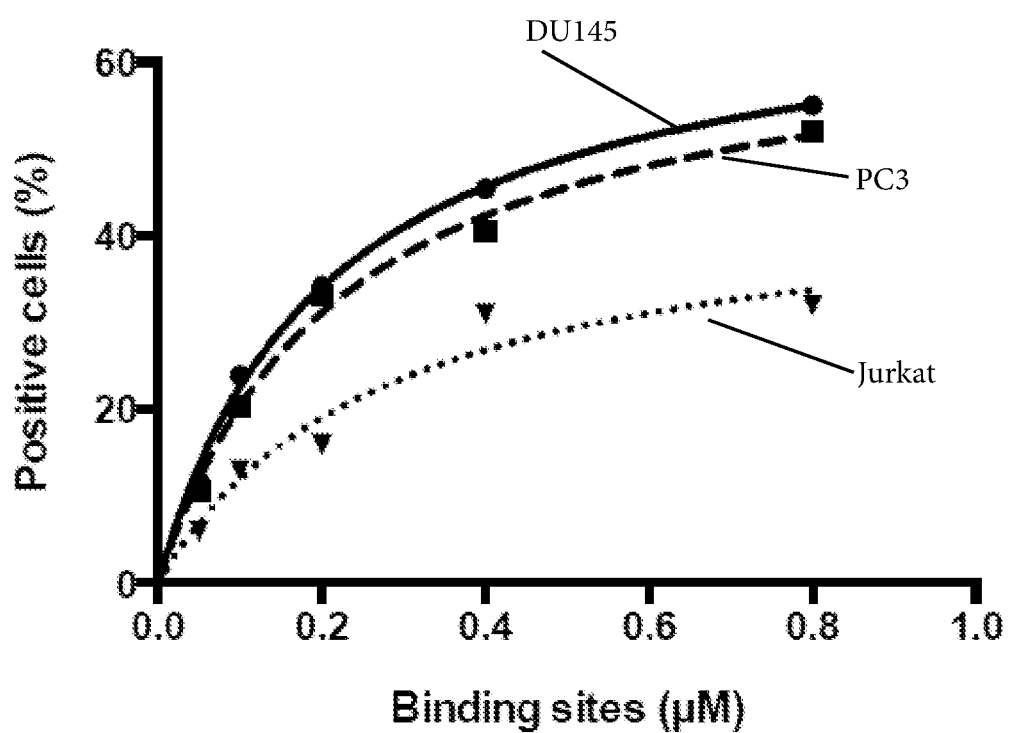
Figure 15:
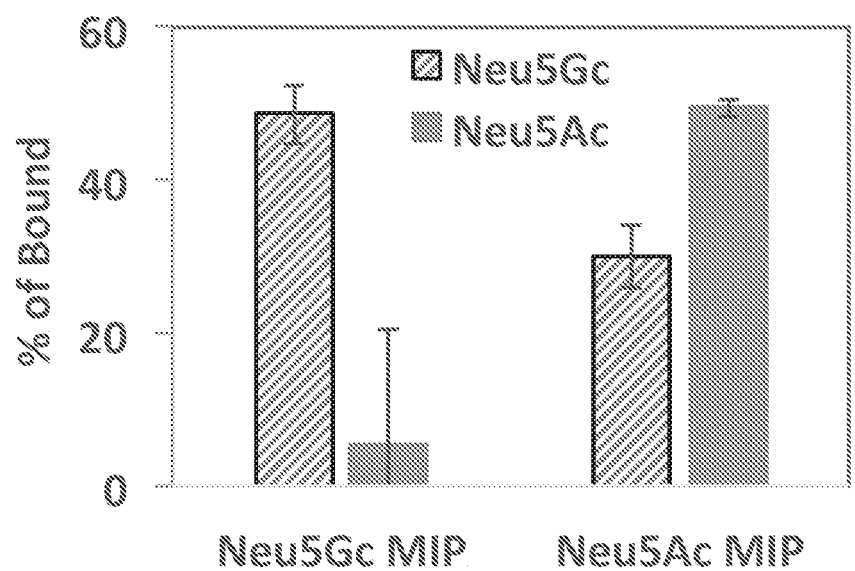
Figure 15:
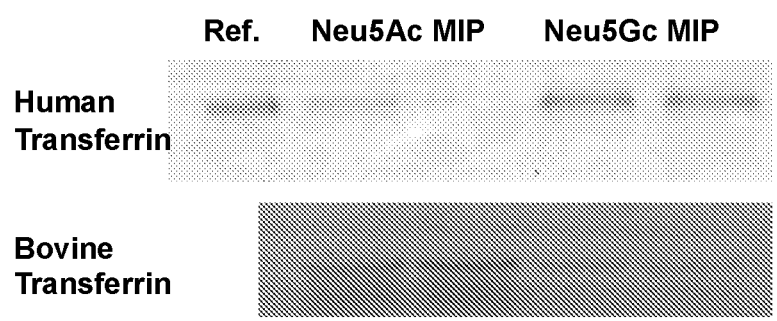
Figure 16:
Figure 16:
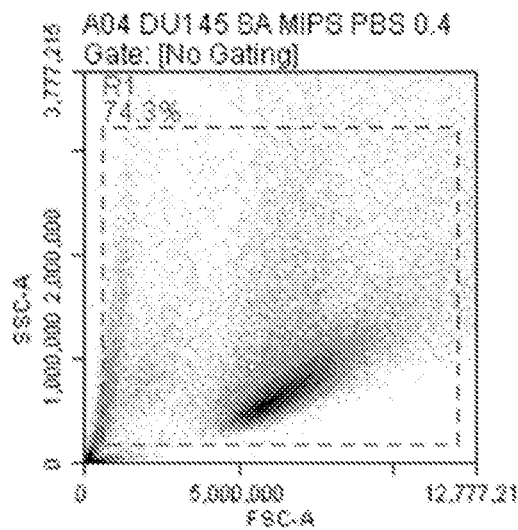
Figure 16:
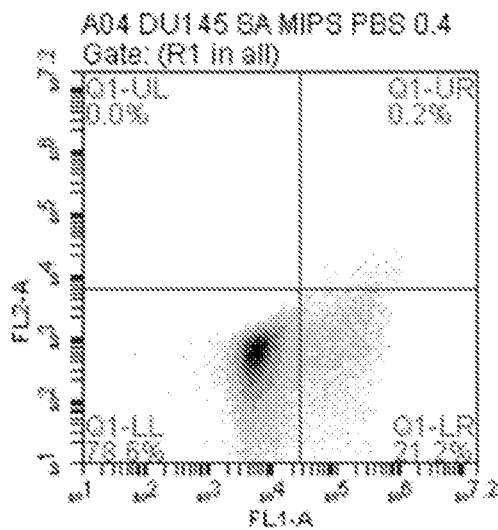
Figure 16:
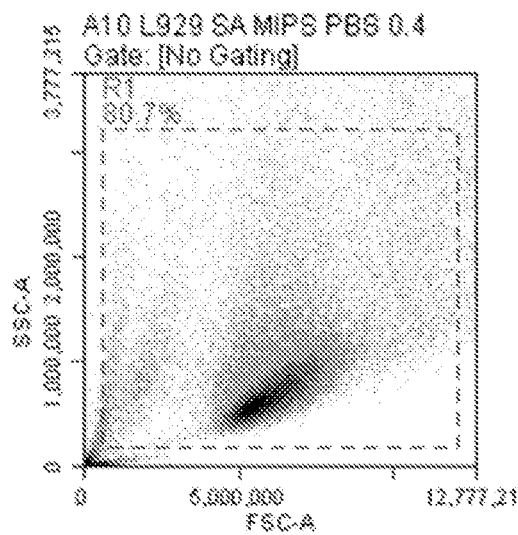
Figure 16:
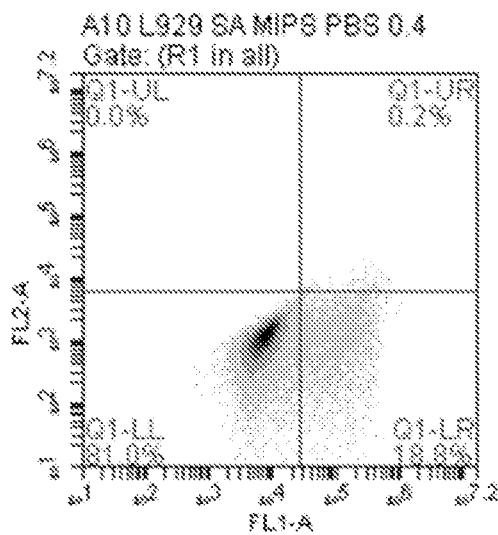
Figure 17:
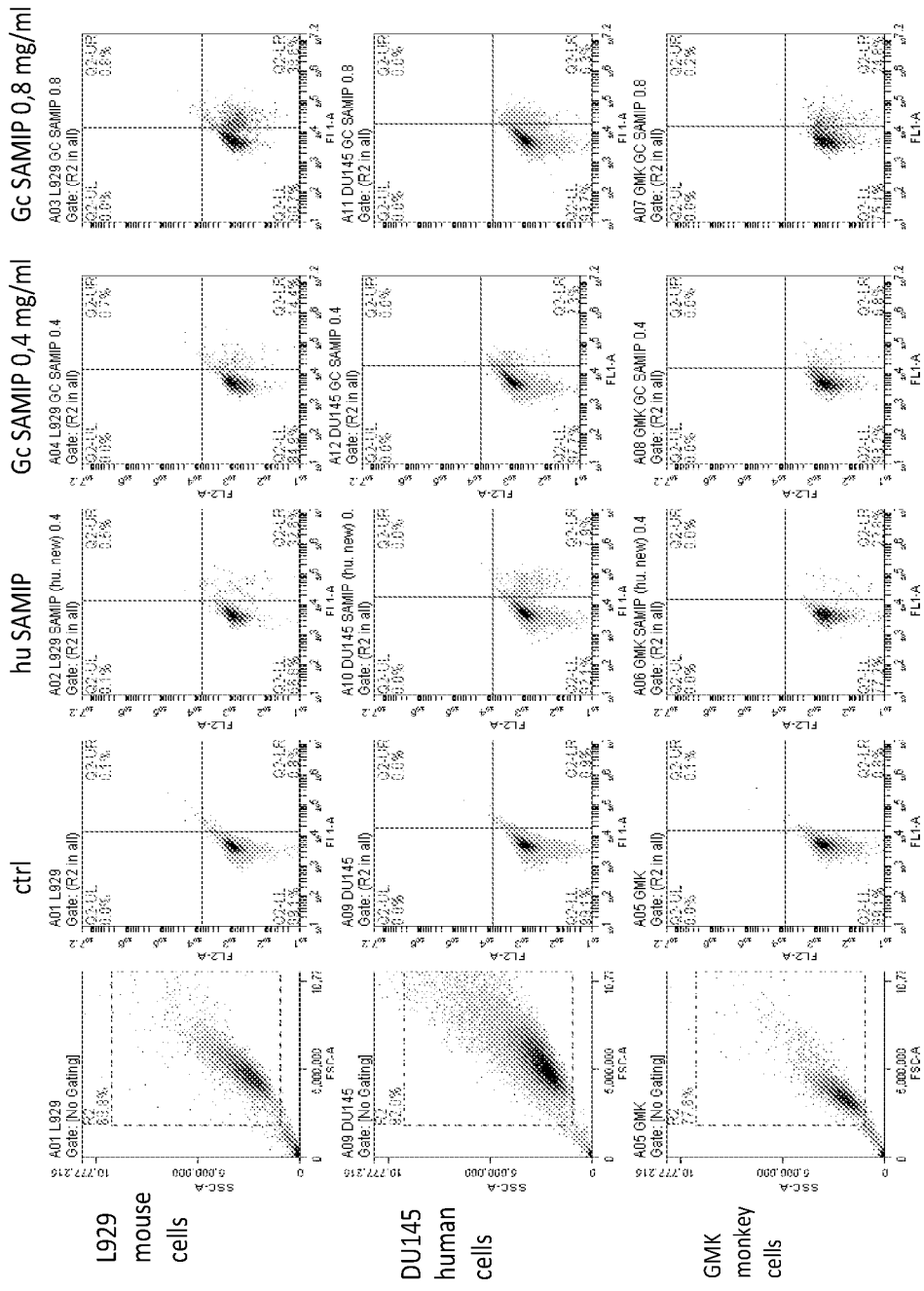
Figure 18:
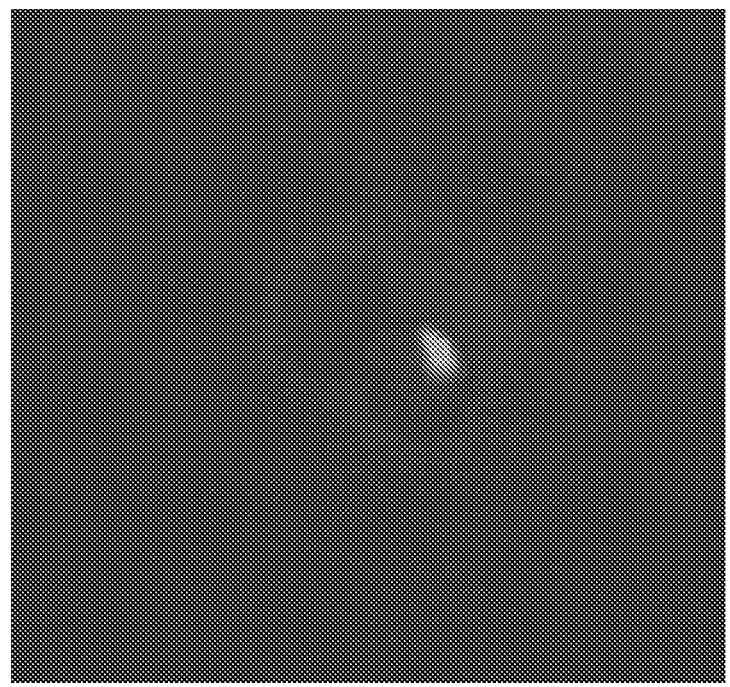
Figure 18:
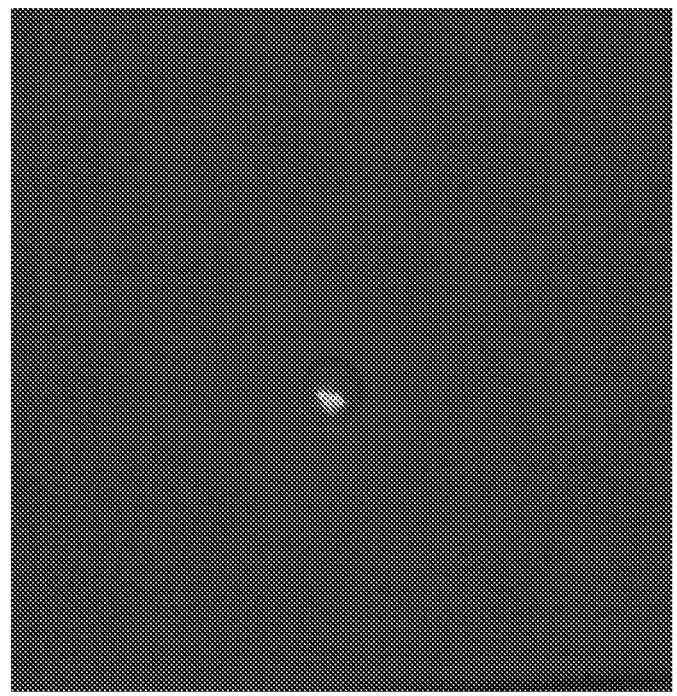
Figure 18:
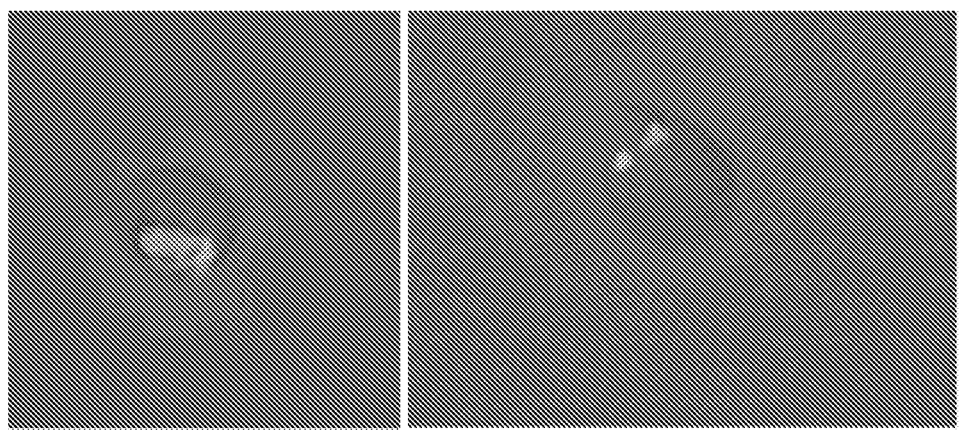
Figure 19:
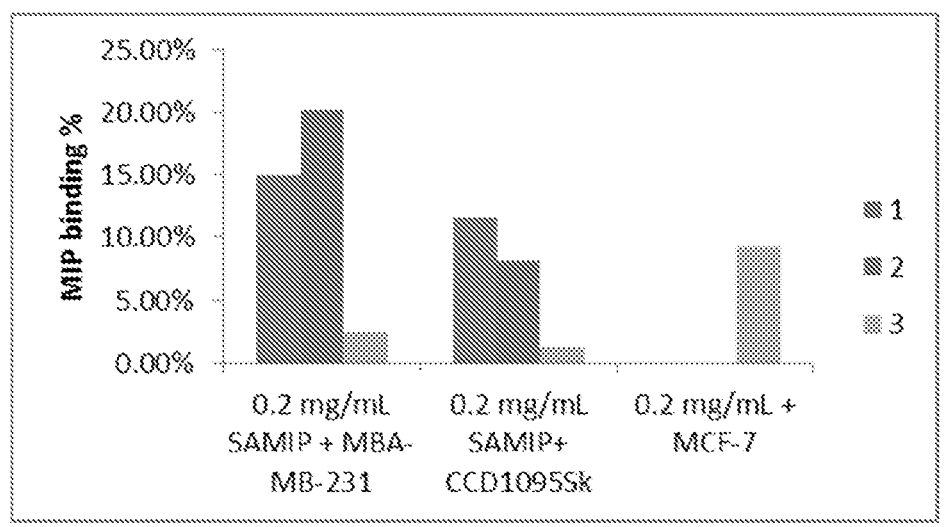
Figure 19:
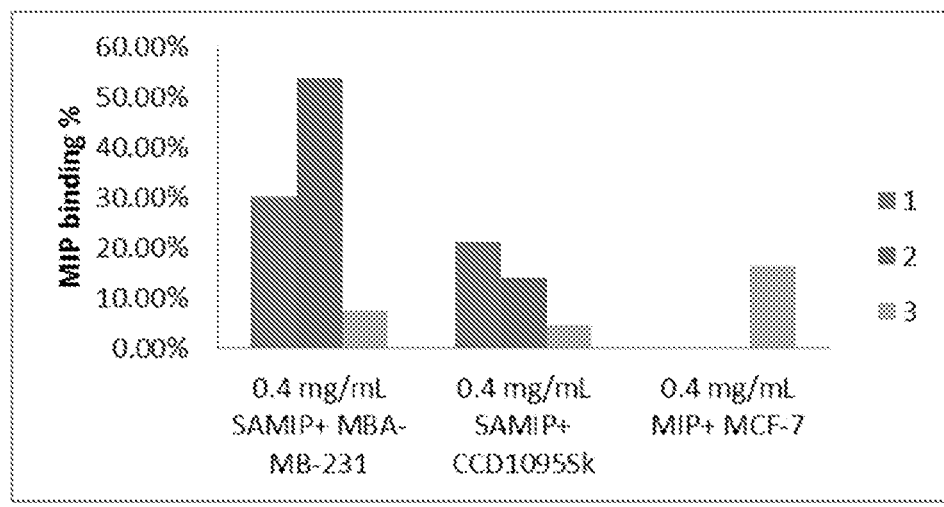

Chart 3. (A) Examples of basic, cationic, acidic or anionic functional monomers. Amine containing monomers are of the general formula $NR_1R_2R_3$ with all groups R directly connected to N where at least one of $R_1$, $R_2$, $R_3$ is a polymerizable group. Examples of amine containing monomers are 2-vinylpyridine (2-VPY), 4-vinylpyridine (4-VPY), diethylaminoethyl methacrylate (DEAEMA), 2-aminoethyl methacrylate (AEMA), 2-aminoethyl methacrylamide (AEMAM), N-vinylimidazole (VIM), N-(dimethyl)-2-ethylmethacrylate (DMAEMA), allylamine (ALAM), p-vinyl-N,N'-diethyl-benzamidine (VDEAB) or p-vinylbenzylamine (VBA). The cationic monomers are of the general formula $NR_1R_2R_3R_4^+X^-$ with all groups R directly connected to N where at least one of $R_1$, $R_2$, $R_3$, $R_4$ is a polymerizable group and $X^-$ is a counteranion. Examples of cationic monomers are N-(trimethyl)-2-ethylmethacrylate-ammonium chloride (TMAEMA), N-(trimethyl)-p-vinylbenzyl-ammonium chloride (TMVBA), N-vinyl-N'-benzyl-imidazolium chloride (VBI), N-vinylpyridinium chloride (N-VPY). Examples of acidic monomers are methacrylic acid (MAA), acrylic acid (AA), trifluoromethylacrylic acid (TFM), itaconic acid (ITA), p-vinylbenzoic acid (PVB), 2-Acrylamido-2-methylpropane sulfonic acid (AMPSA).

(B) Examples of neutral and hydrogen bonding monomers interacting with the saccharide template. Examples of neutral monomers are: N-vinylpyrrolidone (NVP), styrene (S), 2-hydroxyethylmethacrylate (HEMA), acylonitrile (AN), cyanostyrene (CS), N-isopropylacrylamide (NIPAM), acrylamide (AAM), methacrylamide (MAAM), N-tertbutylacrylamide (TBAM). Examples of urea based functional monomers. 1,3 disubstituted urea monomers of the type $R_1$—NHCONH—$R_2$ where at least one of the substituents $R_1$ and $R_2$ is a polymerizable group. Examples of urea based monomers are: 1-(4-styryl)-3-(3,5-trifluoromethyl-phenyl)-urea (TFU).

(C) Examples of crosslinkers: Ethyleneglycoldimethacrylate (EGDMA), divinylbenzene (DVB), trimethylpropanetrimethacrylate (TRIM), pentaerythritoltriacrylate (PETA), ethyl-diacrylamide (EBR), piperazine-diacrylamide (PBA), methylenebisacrylamide (MBA).

(D) Examples of fluorogenic urea based functional monomers with substitutent R as indicated.

(E) Examples of monomers covalently binding the saccharide template where R is a polymerizable group. Examples are boronic acids of the type R—$B(OH)_2$ or R—$B(OH)OR_2$ (where $R_2$ is an alkyl or aryl substituent), hydrazines R—NH—$NH_2$, amines such as benzylamines R-Bzl-$NH_2$ or polyamines, sulfonhydrazides R-$PhSO_2NHNH_2$.

(F) Examples of boronic acid monomers for use in saccharide imprinting.

Chart 4. Typical procedure for preparing a glycan imprinted polymer based on cooperative imprinting. This consisted in RAFT mediated grafting of a SA imprinted shell on silica core particles by a mixed covalent and non-covalent approach including reversible boronate esterification (1), hydrogen bond stabilization and a guest responsive fluorescent reporter group (2) and amine-catalysis and electrostatic stabilization (3).

Chart 5. TEM images of SA (A, B) or GA (C, D) imprinted core shell nanoparticles. Scale bar=0.5 µm (A, C) or 50 nm (B, D).

Chart 6. Transmission FTIR spectra (KBr) of SA-MIP (upper red trace), GA-MIP (middle blue trace) and the RAFT modified core particles (lower black trace).

Chart 7. Binding curves for SA (filled circles) or GA (open triangles) added to the SA-MIP and SA (open circles) and GA (filled triangles) added to the GA-MIP in mixtures of methanol and water containing A) 2% water, B) 50% water, C) 98% water. The binding curves corresponding to SA and GA bound to the SA-MIP were fitted to a Langmuir mono-site model resulting in the binding parameters listed beside the respective graphs. The data corresponding to the GA-MIP was poorly fitted by the Langmuir equation and was not further evaluated.

Chart 8. Fluorescence microscopy images of DU145 cells incubated with SA-MIP 27 µg/ml (A) or 80 µg/ml (B) and with GA-MIP 27 µg/ml (C) or 80 µg/ml (D). Transmission mode images confirmed the number of cells to be similar in A-D. The scale bar represents 2 µm.

Chart 9. Fluorescence microscopy images of DU145 cells incubated in water (2% methanol) with SA-MIP (20 µg/mL) (A) and FITC-lectin (1 µg/mL) (B) after nuclear staining using DAPI ($\lambda_{exc}$=359 nm; $\lambda_{em}$=461 nm). Scale bar=10 µm.

Chart 10. Fluorescence microscopy images of DU145 (A,C) and PC3 (B,D) cells incubated with FITC-lectin (1 µg/mL). C and D are controls recorded in absence of FITC-lectin. The scale bar represents 10 µm.

Chart 11. Flow cytometry based quantification of cellular fluorescence of DU145 cells as a function of added SA-MIP probe (A) or FITC-lectin (B) expressed as percent positive cells.

Chart 12. Flow cytometry based quantification of cellular fluorescence of DU145 and PC3 cells (A, C) and Jurkat cells (B, D) as a function of added SA-MIP probe (A, B) or FITC-lectin (C, D) expressed as percent positive cells.

Chart 13. Fluorescence microscopy images of DU145 cells incubated with SA-MIP 20 µg/ml (A) or pre-treated with sialidase 5 U/ml (B) or 10 U/ml (C) and thereafter incubated with SA-MIP 20 µg/ml. D is a control in absence of both sialidase and SA-MIP. The scale bar represents 10 µm.

Chart 14. Flow cytometry based quantification of cellular fluorescence of DU145 (circles), PC3 (squares) and Jurkat (triangles) cell lines as a function of added SA-MIP probe expressed as binding site concentration (N≈10 µmol/g). Nonlinear curve fitting resulted in binding constants (K) for Jurkat: 3.6 (±1.8)×10$^6$ M$^{-1}$; DU145: 4.8 (±0.4)×10$^6$ M$^{-1}$; PC3: 4.5 (±0.6)×10$^6$ M$^{-1}$.

Chart 15. (A) Bound fraction (% bound) of Neu5Gc and Neu5Ac after incubation in water with a Neu5Ac-MIP or a Neu5Gc-MIP respectively. (B) PAGE of supernatant fractions after depletion of transferrin (bovine or human form) from suspension of either Neu5Ac-MIP or Neu5Gc-MIP.

Chart 16. Staining of live cells using SA-MIPs

Chart 17. Staining of human and animal cell lines using Neu5Ac and Neu5Gc MIPs.

Chart 18. Viable RAW mouse macrophage cells incubated with SAMIPs 1 h (A), 5 h (B), 24 h (C,D) and thereafter analyzed with fluorescence microscopy.

Chart 19. Staining of human breast cancer cell lines of known malignancy using SA-MIPs. MB-231 are more aggressive human breast cancer cells whereas CCD1095Sk are more benign.

DEFINITIONS

"A "polymerisable group" is a group of atoms forming part of a monomer capable of reacting with itself or with other monomers to form a polymer.

"Specific binding" of a MIP mean that the MIP exhibits appreciable affinity for a target or a small group of targets or a preferred epitope and, preferably, does not exhibit significant crossreactivity.

"Nanoparticles" refers to inorganic or organic particles with an average size smaller than 1 µm (particle diameter).

An "Antigen" (Immunobiology) is a substance that evokes the production of antibodies.

An "Assay" is a standardized reaction procedure for the qualitative and quantitative detection of an analyte (pharmaceutics, molecular biology)

"Controlled radical polymerization (CRP)" is a polymerization method in which the determination reaction is reversible, thus allowing to achieve a predetermined molecular weight and narrow molecular weight distributions over a wide range of monomers.

A "Ligand" forms a complex with a biomolecule, usually to serve a biological purpose.

"Molecularly imprinted polymers (MIPs)" Polymer that has been processed using the molecular imprinting technique which leaves cavities in polymer matrix with affinity to a chosen "template" molecule.

"Nanogels/microgel" Nanoparticles or microparticles, respectively, composed of a hydrophilic polymer network.

The "Partition coefficient" is Ratio of concentrations of a compound in a mixture of two immiscible phases at equilibrium, e.g. template bound to MIP and free template in solution.

A "Stationary phase" is a substance fixed in place in a chromatography procedure.

A "Target" in the context of MIPs is the molecule which should be bound by a MIP. This is not necessarily identical with the template (epitope approach). Sialic acid (SA) or sialyl (Sia) can refer to both the human form, N-acetylneuraminic acid (Neu5Ac) and the animal form, N-glycolylneuraminic acid (Neu5Gc), of sialic acid.

DETAILED DESCRIPTION OF THE INVENTION

According to the invention there is provided a molecularly imprinted polymer characterised in that it is obtainable by:
1) providing a saccharide template;
2) providing at least two functional monomers capable of cooperatively interacting with the template
3) providing a crosslinking monomer
4) polymerizing the monomers optionally dissolved in a solvent, in presence of the saccharide template.
5) removing the template from the formed polymer.

In one embodiment, the invention refers to a molecularly imprinted polymer wherein the template is a saccharide being an epitope corresponding at least in part to a cell surface glycan In one embodiment the template is a tumor specific cell surface glycan examplified by the glycans depicted in Chart 2.

In one embodiment the template is a virus specific glycan examplified by the glycans depicted in Chart 2.

In one embodiment the template is Siaα2-6GalNAc (Sialyl Tn)

In one embodiment the template is Siaα 2-3Galβ 1-3GalNAc (Sialyl T)

In one embodiment the template is Siaα 2,3Galβ 1,4 (Fucα 1,3)GlcNAc (Sialyl Lewis X)

In one embodiment the template is Siaα 2,3Galβ 1,3 (Fucα 1,4)GlcNAc (Sialyl Lewis A)

In one embodiment the template is Siaα2,3-Galβ

In one embodiment the template is Siaα2,6-Galβ.

In one embodiment the template is Siaα2,3-N-acetyllactosamine

In one embodiment the template is Siaα2,6-N-acetyllactosamine

In one embodiment the template is N-acetylneuraminic acid (Neu5Ac, human form of sialic acid (SA))

In one embodiment the template is N-glycolylneuraminic acid (Neu5Gc, animal form of sialic acid)

In one embodiment the template is GlcA2SO$_3$β1,4-Glc2NSO$_3$ or GlcA2SO$_3$β1,4-Glc2NSO$_3$6 SO$_3$ In one embodiment the template is sialic acid or a glycan containing one or more sialic acids In one embodiment the template is a monosaccharide In one embodiment the template is a disaccharide In one embodiment the template is a trisaccharide In one embodiment the template is a tretrasaccharide In one embodiment, the invention refers to a molecularly imprinted polymer wherein one of the functional monomers is a monomer capable of forming ion pairs with the template In one embodiment, the invention refers to a molecularly imprinted polymer wherein one of the functional monomers is a monomer of any of the types in Chart 3A, capable of forming ion pairs with the template In one embodiment, the invention refers to a molecularly imprinted polymer wherein one of the functional monomers is 2-aminoethyl-methacrylate.

In one embodiment, the invention refers to a molecularly imprinted polymer wherein one of the functional monomers is a neutral monomer capable of hydrogen bonding with the template In one embodiment, the invention refers to a molecularly imprinted polymer wherein one of the functional monomers is a neutral monomer of any of the types in Chart 3B, capable of hydrogen bonding with the template.

In one embodiment, the invention refers to a molecularly imprinted polymer wherein one of the functional monomers is 2-(-3-(4-nitrobenzo[c][1,2,5] oxadiazo-7-yl)ureido) ethylmethacrylate.

In one embodiment, the invention refers to a molecularly imprinted polymer wherein the crosslinking monomer is any of the types in Chart 3B.

In one embodiment, the invention refers to a molecularly imprinted polymer wherein one of the functional monomers is a monomer capable of covalently interacting with the template.

In one embodiment, the invention refers to a molecularly imprinted polymer wherein one of the functional monomers is a monomer, of any of the types shown in Chart 3C, capable of covalently interacting with the template.

In one embodiment, the invention refers to a molecularly imprinted polymer wherein one of the functional monomers is 4-vinyl benzeneboronic acid.

In one embodiment, the invention refers to a molecularly imprinted polymer wherein the functional monomers are at least three representing all three types of monomers depicted in Chart 3.

In one embodiment, the invention refers to a molecularly imprinted polymer wherein one functional monomer is an amine, one functional monomer is a urea and one functional monomer is a boronic acid.

In one embodiment, the invention refers to a molecularly imprinted polymer wherein one functional monomer is an amine, one functional monomer is a urea and one functional monomer is a boronic acid according to any of structures depicted in Charts 3 and 4.

In one embodiment, the invention refers to a molecularly imprinted polymer wherein one functional monomer is 2-aminoethyl-methacrylate hydrochloride, one functional monomer is 2-(-3-(4-nitrobenzo[c][1,2,5] oxadiazo-7-yl) ureido) ethylmethacrylate and one functional monomer is 4-vinyl benzeneboronic acid.

In one embodiment, the invention refers to a molecularly imprinted polymer wherein one functional monomer is a fluorescent reporter monomer.

In one embodiment, the fluorescent monomer is any of the structures shown in Chart 21.

In one embodiment, the invention refers to a molecularly imprinted polymer wherein one functional monomer is a fluorescent reporter monomer such as 1 in Chart 3 and 2 in Chart 4.

In one embodiment, the invention refers to a surface imprinted polymer.

In one embodiment, the invention refers to a surface imprinted polymer produced by surface initiated polymerization.

In one embodiment, the invention refers to a surface imprinted polymer prepared by any of the procedures referred to as precipitation polymerization, miniemulsion polymerization or grafting from polymerization.

In one embodiment, the invention refers to a surface imprinted polymer prepared by the technique of reversible addition fragmentation chain transfer polymerization (RAFT).

In one embodiment, the invention refers to a surface imprinted polymer prepared by the technique of reversible addition fragmentation chain transfer polymerization (RAFT) where the RAFT groups are converted by aminolysis or radical reactions after the synthesis of the imprinted polymer.

The present invention also provides a process for the preparation of a molecularly imprinted polymer, characterised in that it is obtainable by:
1) providing a saccharide template;
2) providing at least two functional monomers capable of cooperatively interacting with the template
3) providing a crosslinking monomer
4) polymerizing the monomers optionally dissolved in a solvent, in presence of the saccharide template.
5) removing the template from the formed polymer.

The present invention also provides a use of the glycan binding polymers for:
separations including cell separations
study of glycosylation status of cells
blood typing and cell agglutination
histochemical staining
assaying enzymes
sensors for molecular targets in terms of identity and concentration.
assays (e.g. ELISA) of glycan determinants
flow cytometry assays
in vivo or in vitro biomarker imaging or as contrast agent
as detection tool in electrophoresis
as therapeutic agents (e.g. as drugs)
for targeted drug delivery
for inhibition of cell surface interactions
as catalysts In a one embodiment, the MIPs are used in cell or tissue imaging, cell sorting, glycomics and cellular glycosylation biomarker analysis or for applications in medicine for instance for targeted drug delivery or the selective inhibition of cell surface interactions. Thus, in one embodiment, the use of a molecularly imprinted polymer is provided, in cell or tissue imaging in vitro, cell sorting in vitro, glycomics and cellular glycosylation biomarker analysis in vitro or in medicine such as in selective inhibition of cell surface interactions in vitro.

In one embodiment, the MIPs are used for the identification and molecular characterization of circulating tumor cells (CTCs) in cancer patients. In one embodiment of the invention, the MIPs are provided for treatment of cancer. In one embodiment, there is provided a use of a molecularly imprinted polymer as disclosed herein, for identification and molecular characterization of circulating tumor cells (CTCs) in vitro from cancer patients.

In one embodiment, the MIPs exerts a therapeutic action through endocytosis or are used therapeutically for intracellular targeted delivery of drugs through endocytosis. In one embodiment, a molecularly imprinted polymer, is provided for use as a therapeutic through endocytosis or for intracellular targeted delivery of drugs through endocytosis of for selective inhibition of cell surface interactions.

EXAMPLES

Materials

Tetraethyl orthosilicate (TEOS), 3-aminopropyltriethoxysilane (APTES), 4-cyano-4-(thiobenzoylthio)pentanoic acid) (CPDB), ethylene glycol dimethacrylate (EGDMA), triethylamine (TEA) and ethyl chloroformate were obtained from Sigma Aldrich (Steinheim, Germany).

Methanol (MeOH) came from Acros Organics (Geel, Belgium). Acetonitrile (ACN) was obtained from Merck (Darmstadt, Germany). EGDMA were passed through a column of activated basic alumina to remove inhibitor and stored at −20° C. before polymerization. Template sialic acid (N-Acetyl neuraminic acid, SA) and D-Glucuronic acid (GA) were received from Calbiochem and Fluka respectively. Monomers 4-vinyl benzeneboronic acid (1) and 2-aminoethyl-methacrylate hydrochloride (3) were purchased from Sigma Aldrich and Polyscience respectively. 2-(-3-(4-nitrobenzo[c][1,2,5] oxadiazo-7-yl)ureido) ethylmethacrylate (2) was synthesized according to our previously published protocol. The human prostate cancer cell lines, DU145 and PC-3 and the T cell leukemia cell line Jurkat were obtained from LGC Standards, Teddington, Middlesex. Fetal bovine serum (FBS) came from Life Technologies, Paisley, UK. SA-specific *triticum vulgans* lectin and neuraminidase (sialidase) from *Clostridium perfringens* were purchased from Sigma-Aldrich, St. Louis, Mo., USA. The nuclear stain 4',6-diamidino-2-phenylindole (DAPI) was purchased from Molecular probe, USA. Polylysine slides were obtained from WVR, Radnor, Pa., USA.

Apparatus and Methods

HPLC:

The HPLC measurements were carried out on Waters Alliance 2795 separation module equipped with a UV-DAD detector and an autosampler.

NMR:

NMR measurements on an Agilent (Varian) Mercury 400 MHz instrument.

Elemental Analysis:

Carbon and nitrogen contents were determined by elemental analysis at the Department of Organic Chemistry, Johannes Guttenberg Universitat Mainz using a Heraeus CHN-rapid analyser (Hanau, Germany).

Stirring Unit:

Stirring during polymerization was performed using a KS130 basic IKA-instrument (IKA Stauffen, Germany) equipped with a dry block heater.

FT-IR Spectroscopy:

This was performed using an Equinox 55 Spektrometer from Bruker.

TEM:

The transmission electron micrographs were recorded using a Tecnai transmission electron microscope.

Instruments for UV-VIS and Fluorescence Spectroscopy:

UV-Vis was measured using a Specord 210 from Analytik Jena. Fluorescence spectra were registered using a FluoroMax 4 spectrometer from Horiba, Instrument for Fluorescence Microscopy and Flow Cytometry:

The specimens were viewed with an Olympus AX 70 microscope at a magnification of ×20. Flow cytometry was performed on an Accuri C6 Flow Cytometer (BD Accuri C6 Flow Cytometer, N.J., US). The excitation wavelength was 495 nm and the detection wavelength was 519 nm.

Example 1. Synthesis of RAFT Modified Silica Core Particles

Synthesis of Monodisperse SiO$_2$ Nanoparticles (SiNP)

Monodisperse SiO$_2$ nanoparticles (SiNP: 200 nm in diameter) were prepared by using a slightly modified Stöber process. In a typical synthesis operation, two solutions with equal volumes were rapidly mixed to give a total volume of ~250 mL: one solution contained ethanol (114 mL) and TEOS (11.4 mL), while the other contained ethanol (50 mL), water (76.5 mL), and ammonium hydroxide (25 wt % in water, 7.6 mL). The reaction mixture generally turns turbid white as SiO$_2$ particles formed after ~10 min. The reaction was allowed to continue for 6 h at room temperature, with moderate stirring, for full completion (yield 3.5 g). Afterwards, the particles were collected by centrifugation (5000 rpm, 10 min) and washed by repeating redispersion in pure ethanol at least three times.

Synthesis of Amino Modified Silica Nanoparticles (SiNP—NH$_2$)

A suspension (7.00 g, 100 mL) of silica nanoparticles (SiNP) in toluene was added to a three-necked round-bottom flask with stirring for 15 min under nitrogen. Based on the theoretical number of silanol groups on the silica surface (8 µmol/m$^2$) an excess of APTES (1.26 g, 5.71 mmol) was then added and the mixture refluxed overnight at 130° C. under nitrogen protection. The mixture was then cooled to room temperature and added to a large amount of hexanes (500 mL). The particles were recovered by centrifugation at 5000 rpm for 10 min and redispersed in 40 mL of acetone followed by reprecipitation in 300 mL of hexanes. The amino functionalized particles were dispersed directly into 70 mL of THF for subsequent coupling of the RAFT agent.

Synthesis of RAFT Modified Silica Core Particles (SiNP-RAFT)

A solution of CPDB (0.385 g, 1.38 mmol), ethylchloroformate (132 µL, 1.38 mmol) and TEA (192 µL, 1.38 mmol) in THF (50 mL) was added to a three-necked round bottom flask (250 mL), equipped with an overhead stirrer. The solution was purged with nitrogen and cooled in an ethanol-liquid nitrogen bath for 40 minutes at −70° C. After that, 7.00 g (70 mL stock solution) of amino modified silica (SiNP—NH$_2$, 1.38 mmol of amino groups) were added at −10° C. and the reaction was allowed to proceed overnight. After that, hexane (500 mL) was added and the particles collected by centrifugation (5000 rpm, 10 min). Then, they were redispersed in acetone (80 mL), precipitated again in 300 mL of hexane, centrifuged at 5000 rpm during 10 min. The resulting nanoparticles (SiNP-RAFT) were dried under vacuum at room temperature (6.5 g, 93% yield).

Example 2. Synthesis of Core Shell Molecularly Imprinted Polymers Using Sialic Acids (SA: Neu5Ac or Neu5Gc) or Glucuronic Acid (GA) as Templates SiNP-RAFT (400 mg) was suspended in a solution containing Neu5Ac (5.3 mg, 17.1 µmol) or Neu5Gc (5.5 mg, 17.1 µmol) or GA (3.3 mg, 17.1 µmol), 1 (2.5 mg, 17.1 µmol), 23 µl of 25% w/v 3 in water (5.6 mg, 34.1 µmol), 2 (5.7 mg, 17.1 µmol) and EGDMA (128 µL, 678 µmol) dissolved in 12 mL of methanol placed in a 20 mL screw capped scintillation vial. The prepolymerization mixture was subjected to sonication for 30 min followed by purging with nitrogen during 20 min. After that, the initiator ABDV (2.31 mg, 9.3 µmol) was added and the suspension again purged for 5 min with nitrogen. The vial was sealed with silicone insulating tape and then the polymerization was initiated by keeping vials on the preheated heater block at 50° C. using a stirring speed of 480 rpm. The reaction was allowed to proceed for 23 h. The particles were then incubated 4×1 hour in 5 mL of a solution of methanol (80.9%), Formic acid (14.3%), Water (4.8%) followed by 1×30 minutes with methanol (15 mL) with intermediate separation of the particles by centrifugation at 5000 rpm. Finally the particles were dried under vacuum at 50° C. resulting in ca 0.4 g of SA-MIP and GA-MIP respectively. The supernatants were collected and analyzed by reversed phase HPLC for the presence of template. This confirmed the final wash to be free of template. The Neu5Ac imprinted particles were characterised by transmission electron microscopy and transmission FTIR and the results are shown in Charts 5 and 6.

Example 3. Synthesis of Core Shell Molecularly Imprinted Polymers Using Siaα 2-3Galβ 1-3GalNAc (Sialyl T) as Template SiNP-RAFT (400 mg) was suspended in a solution containing Siaα 2-3Galβ 1-3GalNAc (Sialyl T) (15 mg, 17 µmol) 1 (2.5 mg, 17 µmol), 23 µl of 25% w/v 3 in water (5.6 mg, 34.1 µmol), 2 (5.7 mg, 17.1 µmol) and EGDMA (128 µL, 678 µmol) dissolved in 12 mL of methanol placed in a 20 mL screw capped scintillation vial. The prepolymerization mixture was subjected to sonication for 30 min followed by purging with nitrogen during 20 min. After that, the initiator ABDV (2.31 mg, 9.3 µmol) was added and the suspension again purged for 5 min with nitrogen. The vial was sealed with silicone insulating tape and then the polymerization was initiated by keeping vials on the preheated heater block at 50° C. using a stirring speed of 480 rpm. The reaction was allowed to proceed for 23 h. The particles were then incubated 4×1 hour in 5 mL of a solution of methanol (80.9%), Formic acid (14.3%), Water (4.8%) followed by 1×30 minutes with methanol (15 mL) with intermediate separation of the particles by centrifugation at 5000 rpm. Finally the particles were dried under vacuum at 50° C. resulting in ca 0.4 g of MIP. The supernatants were collected and analyzed by reversed phase HPLC for the presence of template. This confirmed the final wash to be free of template.

Example 4. Synthesis of Core Shell Molecularly Imprinted Polymers Using Siaα 2,3Galβ 1,4(Fucα 1,3)GlcNAc (Sialyl Lewis X) as Template SiNP-RAFT (400 mg) was suspended in a solution containing Siaα 2,3Galβ 1,4(Fucα 1,3)GlcNAc (Sialyl Lewis X) (20 mg, 17 µmol) 1 (2.5 mg, 17 µmol), 23 µl of 25% w/v 3 in water (5.6 mg, 34.1 µmol), 2 (5.7 mg, 17.1 µmol) and EGDMA (128 µL, 678 µmol) dissolved in 12 mL of methanol placed in a 20 mL screw capped scintillation vial. The prepolymerization mixture was subjected to sonication for 30 min followed by purging with nitrogen during 20 min. After that, the initiator ABDV (2.31 mg, 9.3 µmol) was added and the suspension again purged for 5 min with nitrogen. The vial was sealed with silicone insulating tape and then the polymerization was initiated by keeping vials on the preheated heater block at 50° C. using a stirring speed of 480 rpm. The reaction was allowed to proceed for 23 h. The particles were then incubated 4×1 hour in 5 mL of a solution of methanol (80.9%), Formic acid (14.3%), Water (4.8%) followed by 1×30 minutes with methanol (15 mL) with intermediate separation of the particles by centrifugation at 5000 rpm. Finally the particles were dried under vacuum at 50° C. resulting in ca 0.4 g of MIP. The supernatants were collected and analyzed by reversed phase HPLC for the presence of template. This confirmed the final wash to be free of template.

Example 5. Synthesis of Core Shell Molecularly Imprinted Polymers Using Sia2,3Galβ 1,3(Fucα 1,4)GlcNAc (Sialyl Lewis A) as Template SiNP-RAFT (400 mg) was suspended in a solution containing Sia2,3Galβ 1,3(Fucα 1,4)GlcNAc (Sialyl Lewis A) (20 mg, 17 µmol) 1 (2.5 mg, 17 µmol), 23 µl of 25% w/v 3 in water (5.6 mg, 34.1 µmol), 2 (5.7 mg, 17.1 µmol) and EGDMA (128 µL, 678 µmol) dissolved in 12 mL of methanol placed in a 20 mL screw capped scintillation vial. The prepolymerization mixture was subjected to sonication for 30 min followed by purging with nitrogen during 20 min. After that, the initiator ABDV (2.31 mg, 9.3 µmol) was added and the suspension again purged for 5 min with nitrogen. The vial was sealed with silicone insulating tape and then the polymerization was initiated by keeping vials on the preheated heater block at 50° C. using a stirring speed of 480 rpm. The reaction was allowed to proceed for 23 h. The particles were then incubated 4×1 hour in 5 mL of a solution of methanol (80.9%), Formic acid (14.3%), Water (4.8%) followed by 1×30 minutes with methanol (15 mL) with intermediate separation of the particles by centrifugation at 5000 rpm. Finally the particles were dried under vacuum at 50° C. resulting in ca 0.4 g of MIP. The supernatants were collected and analyzed by reversed phase HPLC for the presence of template. This confirmed the final wash to be free of template.

Example 6. Synthesis of Core Shell Molecularly Imprinted Polymers Using Siaα2-6GalNAc (Sialyl Tn) as Template SiNP-RAFT (400 mg) was suspended in a solution containing Siaα2-6GalNAc (10 mg, 17 µmol) 1 (2.5 mg, 17 µmol), 23 µl of 25% w/v 3 in water (5.6 mg, 34.1 µmol), 2 (5.7 mg, 17.1 µmol) and EGDMA (128 µL, 678 µmol) dissolved in 12 mL of methanol placed in a 20 mL screw capped scintillation vial. The prepolymerization mixture was subjected to sonication for 30 min followed by purging with nitrogen during 20 min. After that, the initiator ABDV (2.31 mg, 9.3 µmol) was added and the suspension again purged for 5 min with nitrogen. The vial was sealed with silicone insulating tape and then the polymerization was initiated by keeping vials on the preheated heater block at 50° C. using a stirring speed of 480 rpm. The reaction was allowed to proceed for 23 h. The particles were then incubated 4×1 hour in 5 mL of a solution of methanol (80.9%), Formic acid (14.3%), Water (4.8%) followed by 1×30 minutes with methanol (15 mL) with intermediate separation of the particles by centrifugation at 5000 rpm. Finally the particles were dried under vacuum at 50° C. resulting in ca 0.4 g of the MIP. The supernatants were collected and analyzed by reversed phase HPLC for the presence of template. This confirmed the final wash to be free of template.

Example 7. Synthesis of Core Shell Molecularly Imprinted Polymers Using Siaα2,3-Galβ or Siaα2,6-Galβ as Template SiNP-RAFT (400 mg) was suspended in a solution containing Siaα2,3-Galβ or Siaα2,6-Galβ_(10 mg, 17 µmol) 1 (2.5 mg, 17 µmol), 23 µl of 25% w/v 3 in water (5.6 mg, 34.1 µmol), 2 (5.7 mg, 17.1 µmol) and EGDMA (128 µL, 678 µmol) dissolved in 12 mL of methanol placed in a 20 mL screw capped scintillation vial. The prepolymerization mixture was subjected to sonication for 30 min followed by purging with nitrogen during 20 min. After that, the initiator ABDV (2.31 mg, 9.3 µmol) was added and the suspension again purged for 5 min with nitrogen. The vial was sealed with silicone insulating tape and then the polymerization was initiated by keeping vials on the preheated heater block at 50° C. using a stirring speed of 480 rpm. The reaction was allowed to proceed for 23 h. The particles were then incubated 4×1 hour in 5 mL of a solution of methanol (80.9%), Formic acid (14.3%), Water (4.8%) followed by 1×30 minutes with methanol (15 mL) with intermediate separation of the particles by centrifugation at 5000 rpm. Finally the particles were dried under vacuum at 50° C. resulting in ca 0.4 g of the MIP. The supernatants were collected and analyzed by reversed phase HPLC for the presence of template. This confirmed the final wash to be free of template.

Example 8. Synthesis of Core Shell Molecularly Imprinted Polymers Using Siaα2,3-N-Acetyllactosamine or Siaα2,6-N-Acetyllactosamine as Template SiNP-RAFT (400 mg) was suspended in a solution containing Siaα2,3-N-acetyllactosamine or Siaα2,6-N-acetyllactosamine (15 mg) 1 (2.5 mg, 17 µmol), 23 µl of 25% w/v 3 in water (5.6 mg, 34.1 µmol), 2 (5.7 mg, 17.1 µmol) and EGDMA (128 µL, 678 µmol) dissolved in 12 mL of methanol placed in a 20 mL screw capped scintillation vial. The prepolymerization mixture was subjected to sonication for 30 min followed by purging with nitrogen during 20 min. After that, the initiator ABDV (2.31 mg, 9.3 µmol) was added and the suspension again purged for 5 min with nitrogen. The vial was sealed with silicone insulating tape and then the polymerization was initiated by keeping vials on the preheated heater block at 50° C. using a stirring speed of 480 rpm. The reaction was allowed to proceed for 23 h. The particles were then incubated 4×1 hour in 5 mL of a solution of methanol (80.9%), Formic acid (14.3%), Water (4.8%) followed by 1×30 minutes with methanol (15 mL) with intermediate separation of the particles by centrifugation at 5000 rpm. Finally the particles were dried under vacuum at 50° C. resulting in ca 0.4 g of the MIP. The supernatants were collected and analyzed by reversed phase HPLC for the presence of template. This confirmed the final wash to be free of template.

Example 9. Synthesis of Molecularly Imprinted Polymers Using any of Fluorescent Urea Based Monomers as Shown in Chart 3D Example 10. Batch Binding Tests and Adsorption Isotherms Binding tests were performed in order to probe the particles affinity for the saccharide templates. Dry template free particles (20 mg) were suspended in 1 mL of a mixture of methanol and water (2, 50 or 98% water) containing the templates at different concentrations (1-20 µM) in 1.5 mL microfuge tubes. After a 2 h incubation at room temperature by gentle shaking the solutions were centrifuged at 10000 rpm for 15 min. The supernatants were transferred to HPLC vials for measurement of the free solute concentration (F) by reversed phase HPLC analysis, using 20 mM $NaH_2PO_4$ (pH 2.0) as mobile phase, a C-18 reversed phase column (Phenomenex Luna C-18, 250×4.6 mm), a flow rate of 0.7 mL min-1, an injection volume of 20 µl, and the detection performed by UV absorbance measurement at 215 nm. The specific amount of solute bound by the polymeric particles (B) was determined by the following formula:

$$B = \frac{(C_0 - F)v}{m} \quad (1)$$

where $C_0$ is the initial solute concentration, F is the final solute concentration in the supernatant, v (mL) is the total volume of the adsorption mixture, and m is the mass of polymer in each vial. The binding curve was fitted by non-linear regression to a Langmuir mono-site model using the Prism 6 curve fitting software (Graphpad Inc.). See Chart 7 for the binding curves and Table 1 for the binding parameters.

|  | Sialic acid (SA) | | Glucuronic acid (GA) | |
|---|---|---|---|---|
| Water (%) | K ($M^{-1}$) | Bmax (µmol $g^{-1}$) | K ($M^{-1}$) | Bmax (µmol $g^{-1}$) |
| 2 | $6.6 \times 10^5$ | 12.0 | $3.3 \times 10^4$ | 13.3 |
| 50 | $3.5 \times 10^4$ | 9.0 | $2.1 \times 10^4$ | 8.2 |
| 98 | $5.9 \times 10^3$ | 8.4 | $1.8 \times 10^3$ | 10.7 |

Example 11. Cell Cultures

The human prostate cancer cell lines, DU145 and PC-3 were cultured in flasks with Dulbecco's Modified Eagle Medium (DMEM) with 10% FBS and incubated in 37° C. with 5% $CO_2$ in 100% humidity. The T cell leukemia cell line Jurkat was cultured in RPMI 1640 with 10% FBS and garamycin (50 µg/ml) and incubated at 37° C. with 5% $CO_2$ in 100% humidity. The mouse macrophage cell line RAW 264.7 was cultured in RPMI1640 with 10% FBS and penicillin-streptomycin, and the human macrophage cell line THP-1 was cultured in RPMI1640 with 10% FBS and garamycin (50 ug/ml), and incubated in 37° C. with 5% $CO_2$ in 100% humidity. The mouse fibroblast cell line L929 was cultured in DMEM with 10% FBS and glutamine and incubated in 37° C. with 5% $CO_2$ in 100% humidity. The breast cancer cell line CCD1095-Sk was cultured in Eagle's Minimum Essential Medium (MEM) with 10% FBS, MDA-MB231 was cultured in DMEM with 10% FBS, and MCF-7 was cultured in RPMI with 10% FBS and penicillin-streptomycin and incubated in 37° C. with 5% $CO_2$ in 100% humidity.

The adherent cells were passaged by washing with phosphate buffered saline (PBS) and then treated with Trypsin/EDTA, when they reached confluency. For microscopic studies, the cells were cultured in 12-well cell culture plates equipped with round glass cover slips (diameter 12 mm). 10,000 DU145 cells and 20,000 PC-3 cells, respectively, were prepared in 100 µL of cell suspension and pipetted onto each cover slip. After 3 h, 1 mL of cell culture medium was added and the cells were left to grow to reach confluency for at least 48 hours at 37° C. with 5% $CO_2$ in 100% humidity. For microscopy studies of Jurkat cells 100 µl of cell suspension containing 50,000 cells were adhered to poly-lysine slides for 2 hours at 37° C. Thereafter the cells were carefully washed 2× with 100 µl PBS.

Example 12. Cell Fixation, Sialidase Treatment and MIP Staining for Fluorescent Microscopy The cell fixation was performed by washing of the confluent cell containing cover slips 2× with 2 mL PBS followed by incubation for 10 min in 1 mL 4% formaldehyde at room temperature (RT). Fixation was then interrupted by aspirating the formaldehyde from each well followed by washing 3× with 2 mL PBS.

For the SA-MIP and GA-MIP staining, dried MIP particles were suspended in water (3% methanol) by sonication for 4+4 minutes with a VWR ultrasonic cleaner. The stock suspensions were further diluted and sonicated prior to use. After washing of the cells 2× with 2 mL water (3% methanol), 500 µL of the diluted sonicated particle suspension (20 or 80 µg $mL^{-1}$) were added to each well. In addition one negative control lacking the particles was also prepared. The cells were incubated with MIPs for 60 minutes at 37° C. After incubation, the wells were washed 3× with 2 mL water (3% methanol) and the cover slips then prepared for fluorescence microscopy. This was performed by mounting them upside down on the microscope slide using one drop of either mounting medium Prolong® Gold antifade mountant or Prolong® Gold antifade reagent with DAPI (Molecular probe). For typical images of cells stained with MIP particles according to Examples 2-6 see Charts 8 and 9. For treatment with sialidase (neuraminidase from *Clostridium perfringens*), the DU145 cells were washed with Dulbecco's modified Eagle's medium (DMEM) and 200 µL of 5 and 10 U/ml of the enzyme, respectively, was added to the cells for 60 minutes in 37° C. One negative control was left with 200 µL of DMEM only. Thereafter, the cells were washed 3× with DMEM. Afterwards, the cells were washed 2× with 2 mL water (3% methanol) and stained with SA-MIP at a concentration of 20 µg $mL^{-1}$. For typical images comparing treated and untreated cells see Chart 10.

Example 13. Lectin-FITC Staining for Fluorescence Microscopy

Confluent DU145 cells or PC-3 cells grown on cover slips as described above were washed 2× with 2 mL PBS and fixed at RT for 10 minutes in 1 mL 4% formaldehyde. To stop fixation, the formaldehyde was aspirated from each well and washed 3× with 2 mL PBS. The cells were stained with 500 µl of 0.5-1 µg/ml FITC-labeled SA-specific lectin at RT for 60 min and then washed 3× with PBS. Each round glass cover slips was mounted for fluorescent microscopy imaging on a microscopic slide (upside down) with one drop of either mounting medium Prolong® Gold antifade mountant or Prolong® Gold antifade reagent with DAPI (Molecular probe). For typical images see Charts 9 and 11.

Example 14. Flow Cytometry Analysis of MIP and Lectin-FITC $5 \times 10^5$ cells of DU145, PC3, Jurkat or C-I, respectively, were washed 2× with 2 mL PBS and fixed at RT for 20 minutes in 1 mL 4% formaldehyde. After aspiration and washing 3× with PBS, the cells were washed 2× with 2 mL of the incubation solvent (water (3% methanol), doubly distilled water or PBS buffer) and thereafter stained with 500 µL sonicated SA-MIP suspensions at indicated concentrations (5-80 µg $mL^{-1}$) followed by incubation at 37° C. for 60 minutes. After incubation, the cells were washed 3× with 2 mL of the incubation solvent and resuspended in 300 μL of the same solvent and analyzed by flow cytometry.

For flow cytometry analysis of SA-specific lectin, $5 \times 10^5$ cells of DU145, PC3 or Jurkat, respectively, were washed 2× with 2 mL PBS and stained with Lectin-FITC solutions of different concentrations (5-50 ng/mL) and incubated in the dark for 20 min on ice. After the incubation, the cells were washed 2× with PBS and resuspended in 300 μL PBS and analyzed by flow cytometry. For the dependence of % positive cells on added probes see Charts 12 and 13. For the estimation of a binding constant for the MIP probe binding to DU145 see Chart 14.

Example 15. Recognition of Animal and Human Forms of Transferrin Using MIPs Imprinted with Neu5Ac or Neu5Gc 2.5 μg of Human or Bovine transferrin protein was dissolved in 100 μL water and 4 mg Neu5Ac or Neu5Gc imprinted particles (Neu5Ac-MIP and Neu5GcMIP respectively) were suspended in this solution. The suspension was stirred at room temperature for 3 hrs. After centrifugation, 30 μL of the supernatant was taken for polyacrylamide gel electrophoresis (PAGE). The results are shown in Chart 15.

Example 16. Staining of Live Cells Using SA-MIPs

For flow cytometry analysis of SA-MIPs binding to viable cells, $5 \times 10^5$ cells were washed 2× with 2 mL PBS and stained with SA-MIPS dissolved in PBS at different concentrations (0.4-0.8 mg/mL) and incubated at 37° C. for 60 minutes. After the incubation, the cells were washed 2× with PBS and resuspended in 300 μL PBS and analyzed by flow cytometry, and thereafter by fluorescencemicroscopy (see Chart 16).

Example 17. Staining of Human and Animal Cell Lines Using Neu5Ac and Neu5Gc MIPs Human DU145 cells and mouse L929 cells were washed 2× with 2 mL PBS and fixed at RT for 20 minutes in 1 mL 4% formaldehyde. After aspiration and washing 3× with PBS, the cells were washed 2× with 2 mL water (3% methanol) and thereafter stained with 100 μL sonicated Neu5Ac and Neu5Gc MIPs, respectively, at concentrations 20-80 μg mL$^{-1}$) and incubated at 37° C. for 60 minutes. After incubation, the cells were washed 3× with 2 mL water (3% methanol), resuspended in 300 μL methanol/water and analyzed by flow cytometry. For fluorescence microscopy experiments, cells were counterstained with DAPI (Molecular probe) and thereafter analyzed (see Chart 17).

Example 18. Endocytosis Experiments

For flow cytometry analysis of SA-MIPs binding to viable RAW 264.7 cells, $1 \times 10^6$ cells were incubated in 500 ul of medium in 12-well plates. After over night incubation, SA-MIPS dissolved in PBS at different concentrations (0.4-0.8 mg/mL) were added and the cells were incubated at 37° C. for 60 minutes-24 h. After the incubation, the cells were washed 2× with PBS, stained with the lysozome marker Lysotracker for 60 minutes, washed and resuspended in 300 μL PBS and analyzed by fluorescence microscopy for uptake of particles and lysosome activity (see Chart 18).

Example 19. Staining of Human Breast Cancer Cell Lines of Known Malignancy Using SA-MIPs Human breast cancer cell lines CCD1095-Sk (benign), MDA-MB231 (malignant) and MCF-7 (malignant) were washed 2× with 2 mL PBS and fixed at RT for 20 minutes in 1 mL 4% formaldehyde. After aspiration and washing 3× with PBS, the cells were washed 2× with 2 mL water (3% methanol), and thereafter stained with 100 μL sonicated SA-MIPs at concentrations 20-80 μg mL$^{-1}$) and incubated at 37° C. for 60 minutes. After incubation, the cells were washed 3× with 2 mL water (3% methanol), resuspended in 300 μL methanol/water and analyzed by flow cytometry. For fluorescence microscopy experiments, cells were counterstained with DAPI (Molecular probe) and thereafter analyzed (see Chart 19).

Example 20. Staining of Human Brain Tumor Cancer Cell Lines and Skin Cancer (Melanoma) Cell Lines Using SA-MIPs Nine different human brain tumor cancer cell lines and two different melanoma cell lines were washed 2× with 2 mL PBS and fixed at RT for 20 minutes in 1 mL 4% formaldehyde. After aspiration and washing 3× with PBS, the cells were washed 2× with 2 mL water (3% methanol) and thereafter stained with 100 μL sonicated SA-MIPs at concentrations 20-80 μg mL$^{-1}$) and incubated at 37° C. for 60 minutes. After incubation, the cells were washed 3× with 2 mL water (3% methanol), resuspended in 300 μL methanol/water and analyzed by flow cytometry.

The invention claimed is:

1. A molecularly imprinted polymer characterised in that it is obtainable by:
    a) providing a saccharide template;
    b) providing at least two functional monomers capable of cooperatively interacting with the template;
    c) providing a crosslinking monomer;
    d) polymerizing the monomers optionally dissolved in a solvent, in presence of the saccharide template;
    e) removing the template from the formed polymer.

2. A molecularly imprinted polymer according to claim 1, wherein the template is a saccharide being an epitope corresponding at least in part to a cell surface glycan.

3. A molecularly imprinted polymer according to claim 1, wherein the template is a tumor specific cell surface glycan selected from
    an O-glycan comprising:
        Tn antigen selected from GalNAcalpha-O—R;
        TF-antigen selected from Galbeta1-3GalNAc-O—R;
        sTn antigen selected from Neu5Acalpha2-6GalNAcalpha-O—R;
    a Lewis structure comprising:
        Lewis$^y$ selected from [Fuc(alpha1-2)]Gal(beta1-4)[Fuc(alpha1-3)]GlcNAc(beta1-3)Gal;
        Lewis$^x$ selected from Gal(beta1-4)[Fuc(alpha1-3)]GlcNAc(beta1-3)Gal;
        Sialyl Lewis$^x$ selected from [Neu5Ac(alpha2-3)]Gal(beta1-4)[Fuc(alpha1-3)]GlcNAc(beta1-3)Gal;
        Sialyl Lewis$^a$ selected from [Neu5Ac(alpha2-3)]Gal(beta)[Fuc(alpha1-4)]GlcNAc(beta1-3)Gal;
        Lewis$^a$ selected from Gal(beta1-3)[Fuc(alpha1-4)]GlcNAc(beta1-3)Gal; or
        Lewis$^b$ selected from [Fuc(alpha1-2)]Gal(beta1-3)[Fuc(alpha1-4)]GlcNAc(beta1-3)Gal;

a globoside comprising:
Globo H selected from [Fuc(alpha1-2)]Gal(beta1-3)GalNAc(beta1-3)Gal(alpha1-4)Gal(beta1-4)Glc; and SSEA4, i.e. [Neu5Ac(alpha2-3)]Gal(beta1-3)GalNAc(beta1-3)Gal(alpha1-4)Gal(beta1-4)Glc"
a ganglioside comprising:
GD2 selected from GalNAc(beta1)[Neu5Ac(alpha2-8)Neu5Ac(alpha2-3)]Gal(beta1-4)Glc;
GD3 selected from Neu5Ac(alpha2-8)Neu5Ac(alpha2-3)Gal(beta1-4)Glc(beta); or
GM3 selected from Neu5Ac(alpha2-3)Gal(beta1-4)Glc(beta); and
a P blood group related antigen comprising:
P$^k$ selected from Gal(alpha1-4)Gal(beta1-4)Glc; or
P$_1$ selected from Gal(alpha1-3)Gal(beta1-4)GalNAc(beta1-3)Gal(beta1-4)Glc(beta).

4. A molecularly imprinted polymer according to claim 1, wherein the template is a virus specific glycan selected from an O-glycan comprising:
Tn antigen selected from GalNAcalpha-O—R;
TF-antigen selected from Galbeta1-3GalNAc;
sTn antigen selected from Neu5Acalpha2-6GalNAcpha-O—R;
a Lewis structure comprising:
Lewis$^y$ selected from [Fuc(alpha1-2)]Gal(beta1-4)[Fuc(alpha1-3)]GlcNAc(beta1-3)Gal;
Lewis$^x$ selected from Gal(beta1-4)[Fuc(alpha1-3)]GlcNAc(beta1-3)Gal;
Sialyl Lewis$^x$ selected from [Neu5Ac(alpha2-3)]Gal(beta1-4)[Fuc(alpha1-3)]GlcNAc(beta1-3)Gal;
Sialyl Lewis$^a$ selected from [Neu5Ac(alpha2-3)]Gal(beta1-3)[Fuc(alpha1-4)]GlcNAc(beta1-3)Gal;
Lewis$^a$ selected from Gal(beta1-3)[Fuc(alpha1-4)]GlcNAc(beta1-3)Gal; or
Lewis$^b$ selected from, [Fuc(alpha1-2)]Gal(beta1-3)[Fuc(alpha1-4)]GlcNAc(beta1-3)Gal;
a globoside comprising:
Globo H selected from [Fuc(alpha1-2)]Gal(beta1-3)GalNAc(beta1-3)Gal(alpha1-4)Gal(beta1-4)Glc; or
SSEA4, i.e. [Neu5Ac(alpha2-3)]Gal(beta1-3)GalNAc(beta1-3)Gal(alpha1-4)Gal(beta1-4)Glc"
a ganglioside comprising:
GD2 selected from GalNAc(beta1-4)[Neu5Ac(alpha2-8)Neu5Ac(alpha2-3)]Gal(beta1-4)Glc;
GD3 selected from Neu5Ac(alpha2-8)Neu5Ac(alpha2-3)Gal(beta1-4)Glc(beta); or
GM3 selected from Neu5Ac(alpha2-3)Gal(beta1-4)Glc(beta); and
a P blood group related antigen comprising:
P$^k$ selected from Gal(alpha1-4)Gal(beta1-4)Glc; or
P$_1$ selected from Gal(alpha1-3)Gal(beta1-4)GalNAc(beta-Gal(beta1-4)Glc(beta).

5. A molecularly imprinted polymer according to claim 1, wherein the template is Siaα2-6GalNAc (Sialyl Tn, namely Neu5Ac(alpha2-6)GalNAc), Siaα 2-3Galβ 1-3GalNAc (Sialyl T, namely Neu5Ac(alpha2-3)Gal(beta1-3)GalNAc), Siaα2,3Galβ 1,4(Fucα 1,3)GlcNAc (Sialyl Lewis X, namely [Neu5Ac(alpha2-3)]Gal(beta1-4)[Fuc(alpha1-3)]GlcNAc(beta1-3)Gal), Sia2,3Galß 1,3(Fucα 1,4)GlcNAc (Sialyl Lewis A, namely [Neu5Ac(alpha2-3)]Gal(beta1-3)[Fuc(alpha1-4)]GlcNAc(beta1-3)Gal), Siaα2,3-Galβ (namely Neu5Ac(alpha2-3)Gal(beta)), Siaα2,6-Gap (namely Neu5Ac(alpha2-6)Gal(beta)), Siaα2,3-N-acetyllactosamine (namely Neu5Ac(alpha2-3)Gal(beta1-4)GlcNAc), Siaα2,6-N-acetyllactosamine (namely Neu5Ac(alpha2-6)Gal(beta1-4)GlcNAc), N-acetylneuraminic acid namely Neu5Ac which is human form of sialic acid, N-glycolylneuraminic acid (Neu5Gc, namely Neu5Gc which is animal form of sialic acid), GlcA2SO3β1,4-Glc2NSO$_3$ or GlcA2S03β1,4-Glc2NS036S03, wherein Sia represents sialyl, GalNAc indicates N-Acetylgalactosamine, Gal represents galactose, Fuc represents fucose, GlcNAc represents N-Acetylglucosamine, and Glc represents glucose, GlcA2S03 represents 2-O-sulfated glucuronic acid, Glc2NSO3 represents 2-N-sulfated glucose-2-amine, and Glc2NS036S03 represents 2-N-sulfated-6-O-sulfated glucose-2-amine.

6. A molecularly imprinted polymer according to claim 1, wherein the template is sialic acid or a glycan containing one or more sialic acids.

7. A molecularly imprinted polymer according to claim 1, wherein the template is a monosaccharide, disaccharide, trisaccharide or tetrasaccharide.

8. A molecularly imprinted polymer according to claim 1, wherein one of the functional monomers is a monomer capable of forming ion pairs with the template.

9. A molecularly imprinted polymer according to claim 8, wherein one of the functional monomers is a monomer of any of the types depicted below

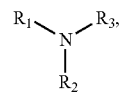

i.e. a monomer containing amino groups, wherein at least one of R$_1$, R$_2$, R$_3$ is a polymerizable group,

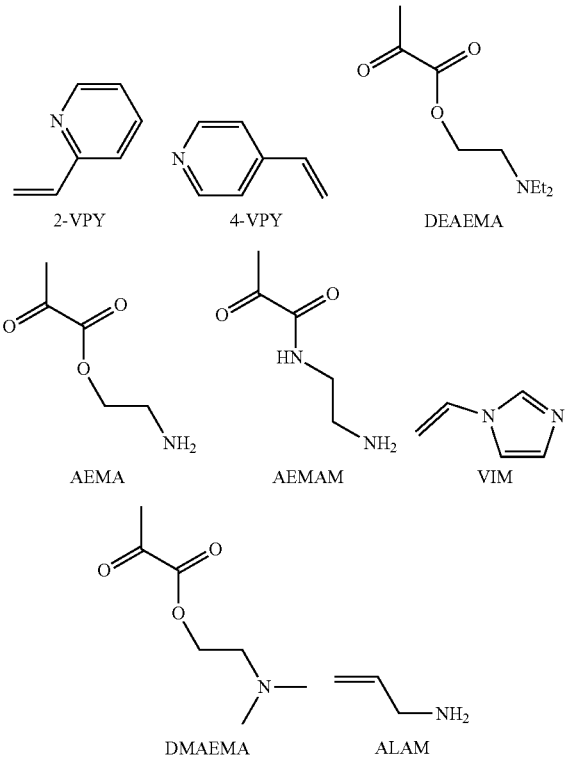

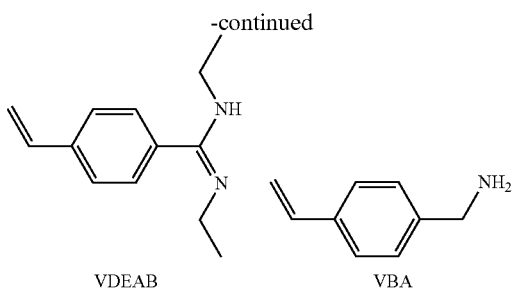

VDEAB      VBA

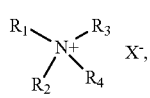

i.e. a cationic monomer containing amino groups, wherein at least one of $R_1$, $R_2$, $R_3$ and $R_4$ is a polymerizable group,

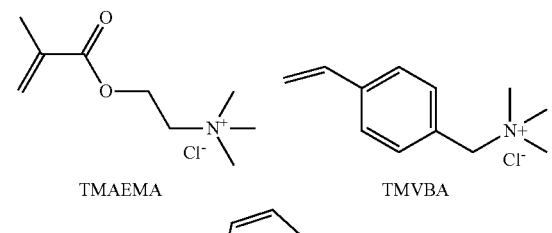

TMAEMA      TMVBA

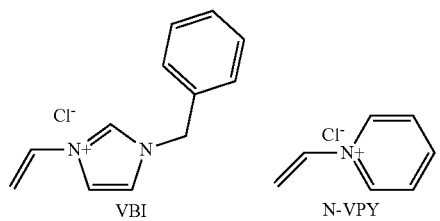

VBI      N-VPY acidic monmers:

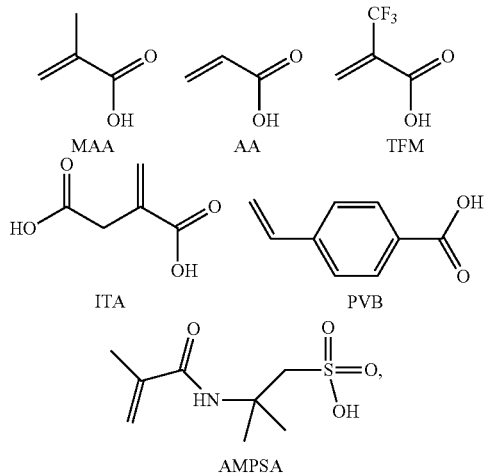

which are capable of forming ion pairs with the template; or selected from a substance having the general formula $NR_1R_2R_3$, wherein $R_1$, $R_2$, and $R_3$ are directly connected to N and wherein at least one of $R_1$, $R_2$, and $R_3$ is a polymerizable group; or selected from 2-vinylpyridine (2-VPY), 4-vinylpyridine (4-VPY), diethylaminoethyl methacrylate (DEAEMA), 2-aminoethyl methacrylate (AEMA), 2-aminoethyl methacrylamide (AEMAM), N-vinylimidazole (VIM), N-(dimethyl)-2-ethylmethacrylate (DMAEMA), allylamine (ALAM), p-vinyl-N,N'-diethyl-benzamidine (VDEAB), and p-vinylbenzylamine (VBA);
or selected from a cationic monomer of the general formula $NR_1R_2R_3R_4^+X^-$ with all groups R directly connected to N where at least one of $R_1$, $R_2$, $R_3$, $R_4$ is a polymerizable group and $X^-$ is a counteranion;
or selected from a cationic monomers selected from: N-(trimethyl)-2-ethylmethacrylate-ammonium chloride (TMAEMA), N-(trimethyl)-p-vinylbenzyl-ammonium chloride (TMVBA), N-vinyl-N'-benzyl-imidazolium chloride (VBI), and N-vinylpyridinium chloride (N-VPY);
or selected from an acidic monomerselected from: methacrylic acid (MAA), acrylic acid (AA), trifluoromethylacrylic acid (TFM), itaconic acid (ITA), p-vinylbenzoic acid (PVB), and 2-Acrylamido-2-methylpropane sulfonic acid (AMPSA).

10. A molecularly imprinted polymer according to claim 1, wherein one of the functional monomers is 2-aminoethylmethacrylate.

11. A molecularly imprinted polymer according to claim 1, wherein one of the functional monomers is a neutral monomer capable of hydrogen bonding with the template.

12. A molecularly imprinted polymer according to claim 11, wherein the neutral monomer is selected from the types depicted below neutral monomers:

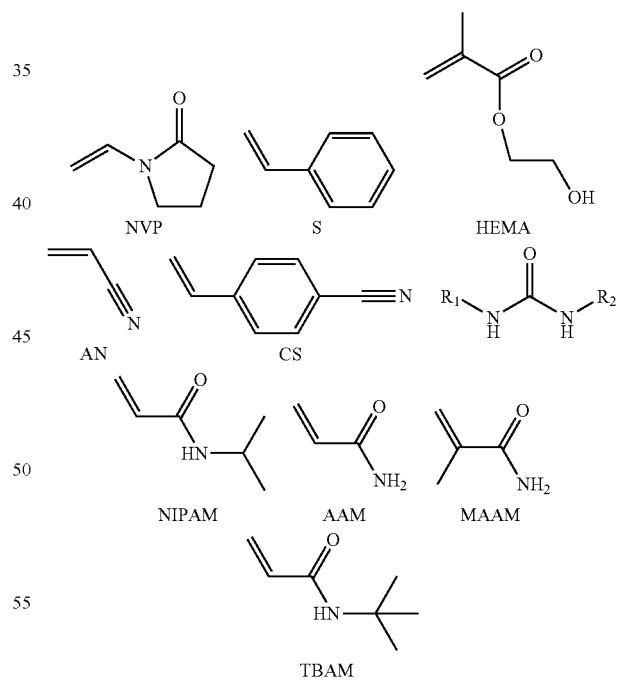

which are capable of hydrogen bonding with the template; or selected from: N-vinylpyrrolidone (NVP), styrene (S), 2-hydroxyethylmethacrylate (HEMA), acylonitrile (AN), cyanostyrene (CS), N-isopropylacrylamide (NIPAM), acrylamide (AAM), methacrylamide (MAAM), and N-tertbutylacrylamide (TBAM).

13. A molecularly imprinted polymer according to claim 11, wherein one of the functional monomers is a 1,3 disubstituted urea monomers of the type R₁—NHCONH—R₂ where at least one of the substituents R₁ and R₂ is a polymerizable group;

or one of the functional monomers is a structure selected from the structures shown below

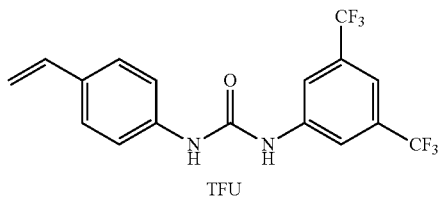
TFU

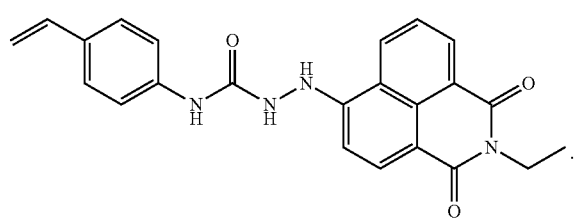

14. A molecularly imprinted polymer according to claim 1, wherein one of the functional monomers is 2-(-3-(4-nitrobenzo[c][1,2,5] oxadiazo-7-yl)ureido) ethylmethacrylate or 1-(4-styryl)-3-(3,5-trifluoromethyl-phenyl)-urea (TFU) or any of the types depicted below

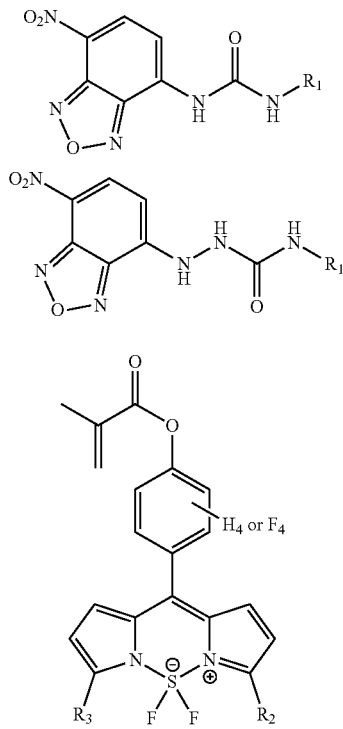

-continued

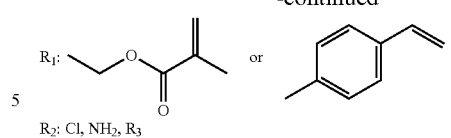

R₂: Cl, NH₂, R₃

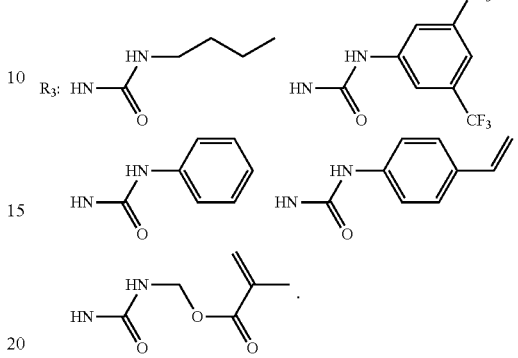

R₃:

15. A molecularly imprinted polymer according to claim 1, wherein the crosslinking monomer is selected from any of the types depicted below crosslinking monomers:

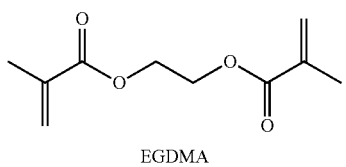
EGDMA

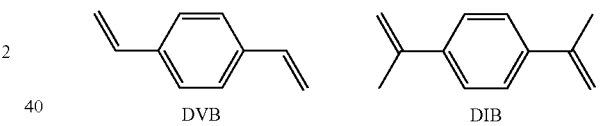
DVB      DIB

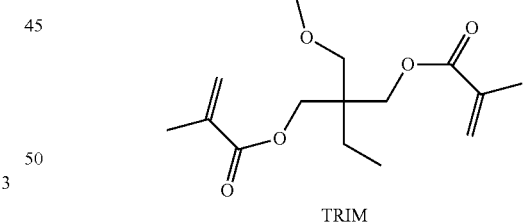
TRIM

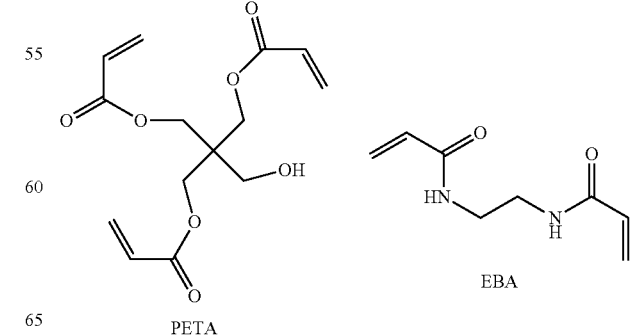
PETA      EBA

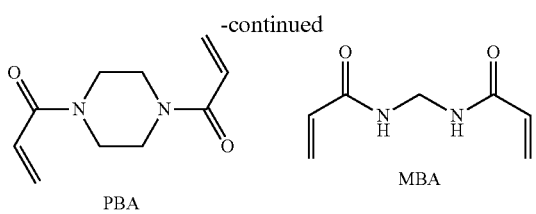

PBA     MBA or selected from: ethyleneglycoldimethacrylate (EGDMA), divinylbenzene (DVB), 1,4-diisopropenylbenzene (DIB), trimethylpropanetrimethacrylate (TRIM), pentaerythritol-triacrylate (PETA), ethyl-diacrylamide (EBA), piperazine-diacrylamide (PBA), and methylenebisacrylamide (MBA).

16. A molecularly imprinted polymer according to claim 1, wherein one of the functional monomers is a monomer capable of covalently interacting with the template.

17. A molecularly imprinted polymer according to claim 16, wherein one of the functional monomers is a monomer, of any of the types depicted below

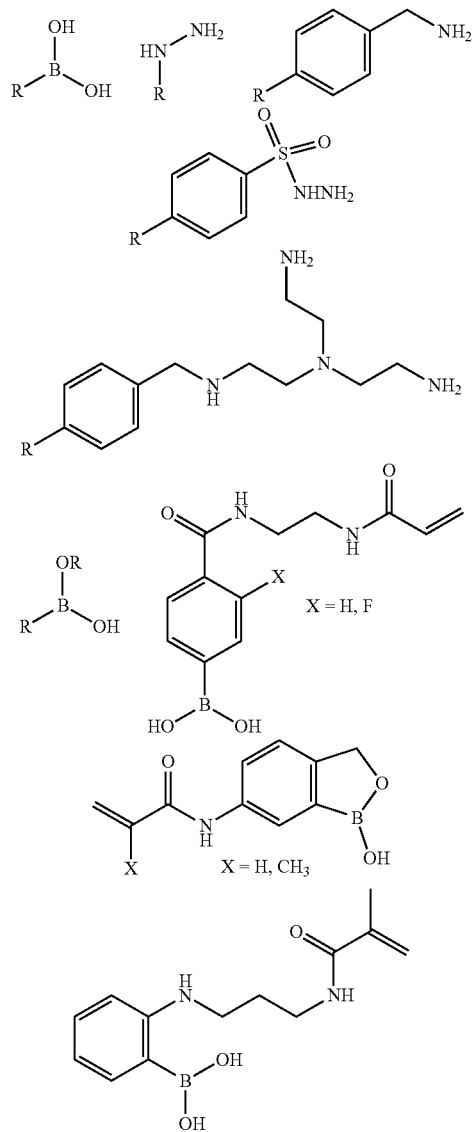

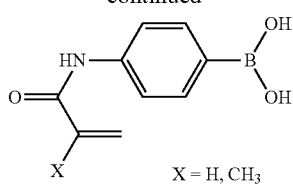

X = H, CH$_3$

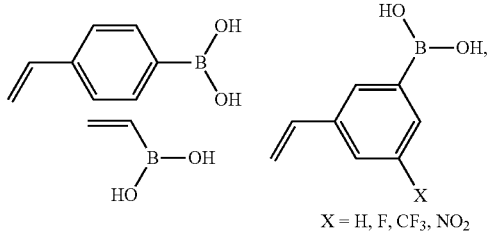

X = H, F, CF$_3$, NO$_2$ which are capable of covalently interacting with the template; or selected from: R—B(OH)$_2$ and R—B(OH)OR$_2$ (where R$_2$ is an alkyl or aryl substituent), hydrazines R—NH-NH$_2$, amines such as benzylamines R-Bzl-NH$_2$ or polyamines, and Sulfonhydrazides R-PhSO$_2$NHNH$_2$.

18. A molecularly imprinted polymer according to claim 17, wherein one of the functional monomers is 4-vinyl benzeneboronic acid.

19. A molecularly imprinted polymer according to claim 1, wherein the functional monomers are at least three representing all three types of monomers depicted below

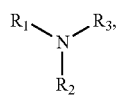

i.e. a monomer containing amino groups, wherein at least one of R$_1$, R$_2$, R$_3$ is a polymerizable group,

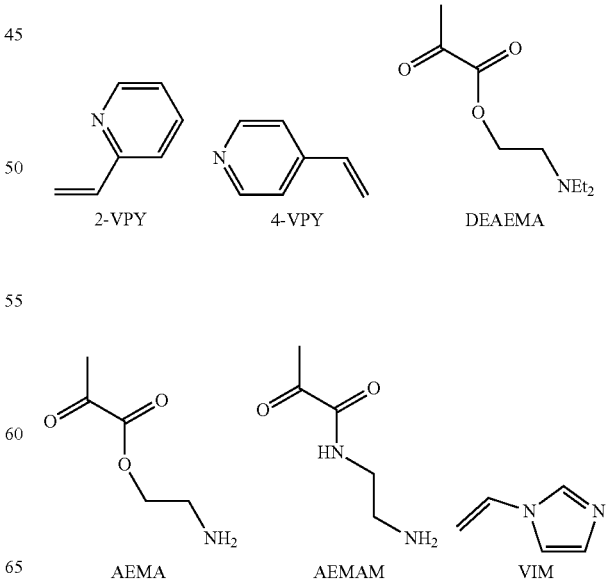

2-VPY    4-VPY    DEAEMA

AEMA    AEMAM    VIM

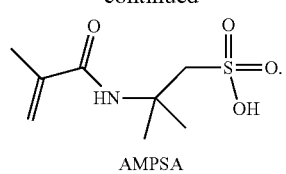

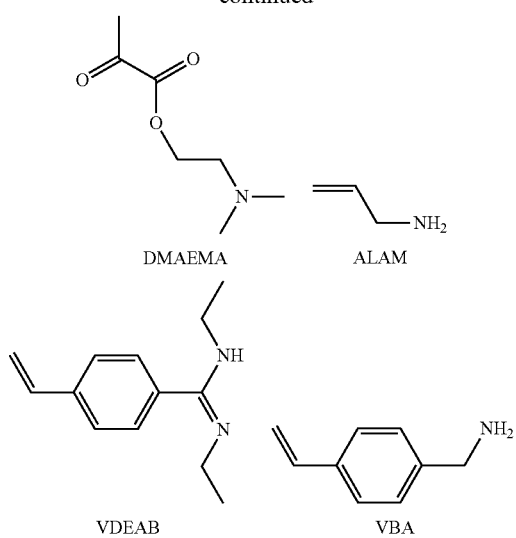

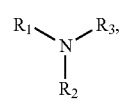

i.e., a cationic monomer containing amino groups, wherein at least one of $R_1$, $R_2$, $R_3$ and $R_4$ is a polymerizable group,

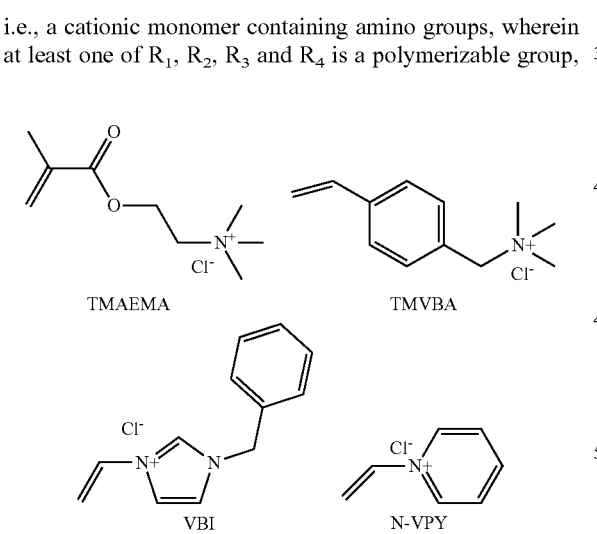

acidic monmers:

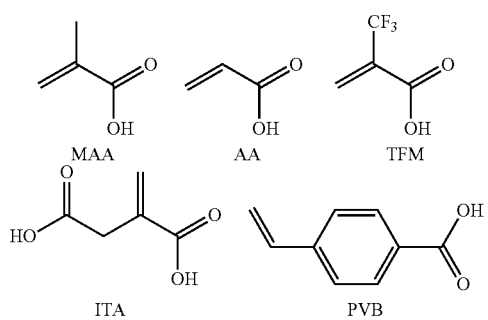

20. A molecularly imprinted polymer according to claim 1, wherein one functional monomer is an amine, one functional monomer is a urea and one functional monomer is a boronic acid.

21. A molecularly imprinted polymer according to claim 1, wherein one functional monomer is an amine, one functional monomer is a urea and one functional monomer is a boronic acid according to any of the structures depicted below i.e. monomer containing amino groups, wherein at least one of $R_1$, $R_2$, $R_3$ is a polymerizable group,

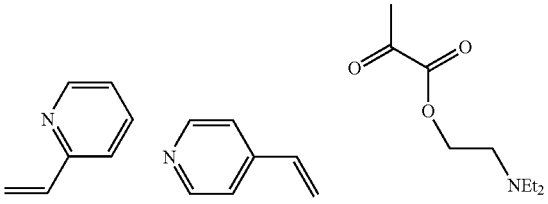

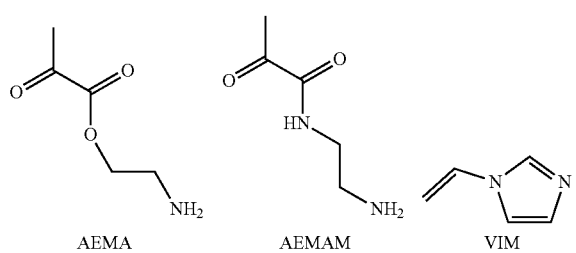

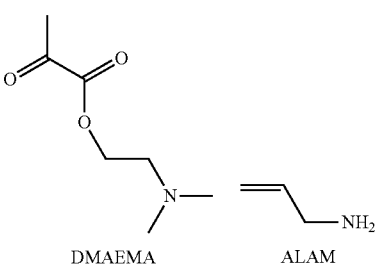

-continued

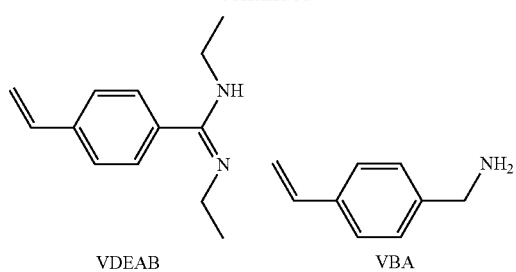

VDEAB     VBA

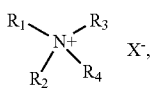

i.e. a cationic monomer containing amino groups, wherein at least one of $R_1$, $R_2$, $R_3$ and $R_4$ is a polymerizable group,

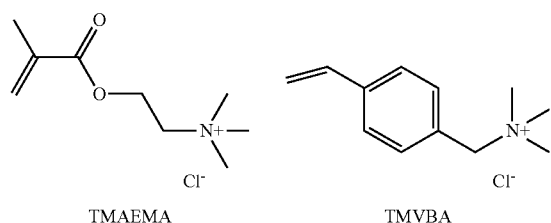

TMAEMA     TMVBA

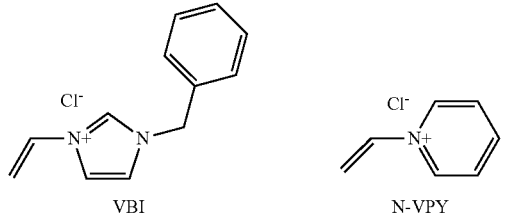

VBI     N-VPY acidic monomers:

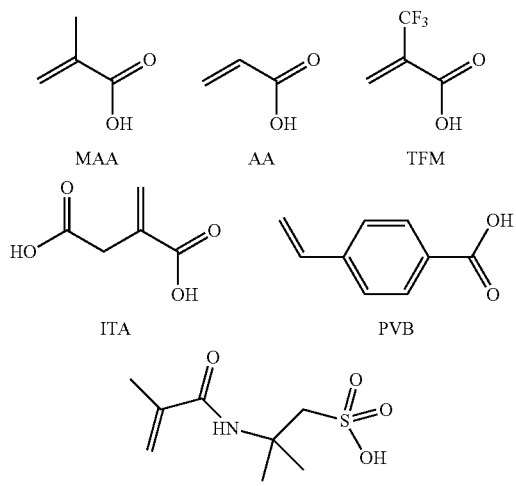

MAA    AA    TFM

ITA     PVB

AMPSA

-continued neutral monomers:

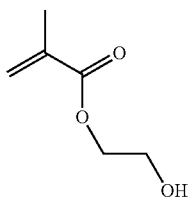

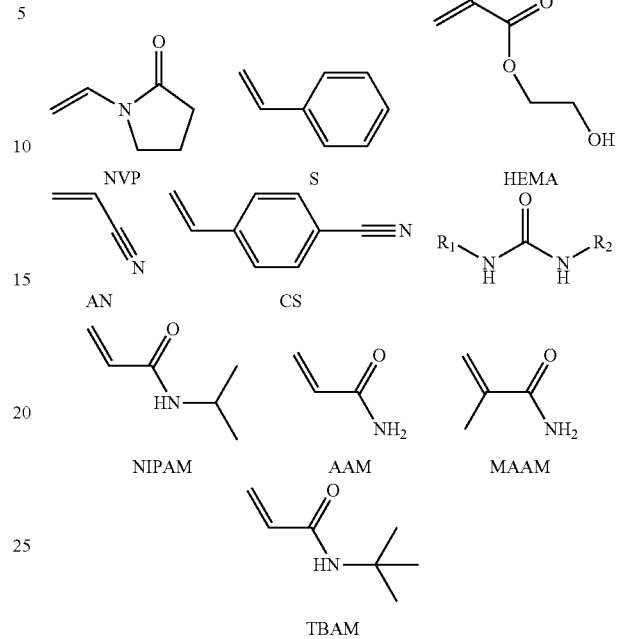

NVP    S    HEMA

AN    CS

NIPAM    AAM    MAAM

TBAM 1,3-disubstituted urea monomers, wherein at least one of the substituents $R_1$ and $R_2$ is a polymerizable group,

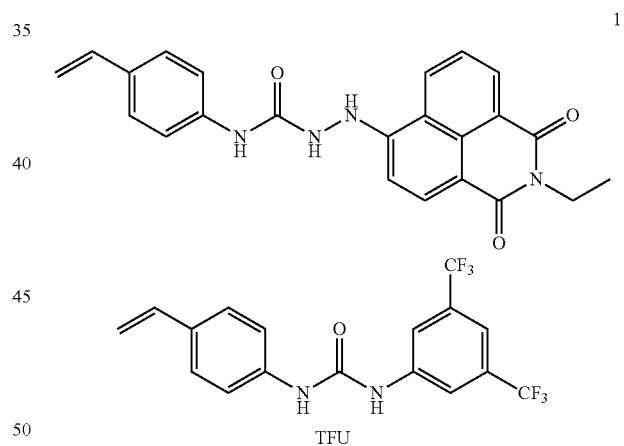

TFU crosslinking monomers:

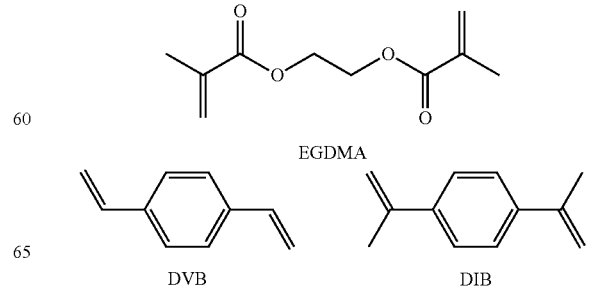

EGDMA

DVB     DIB

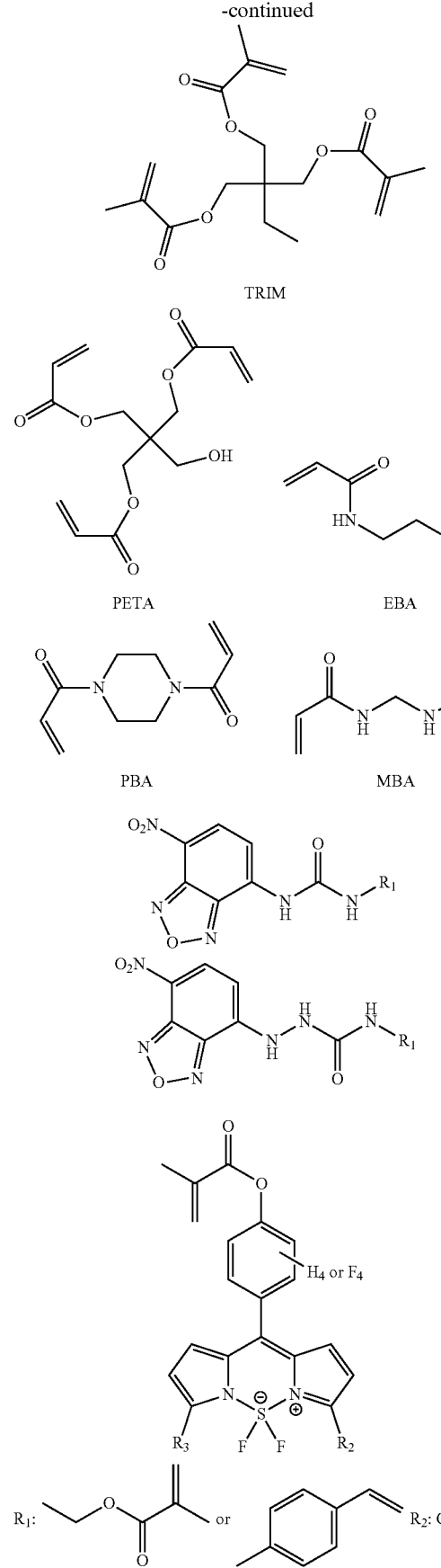

-continued

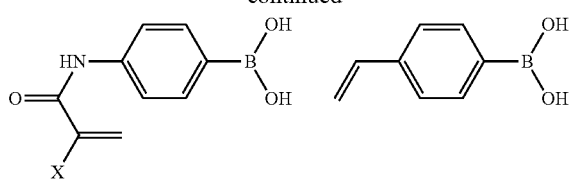

X = H, CH₃

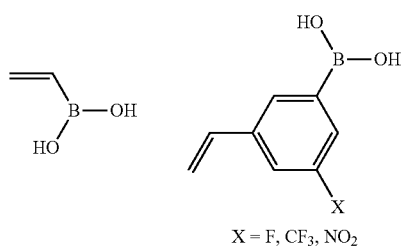

X = F, CF₃, NO₂

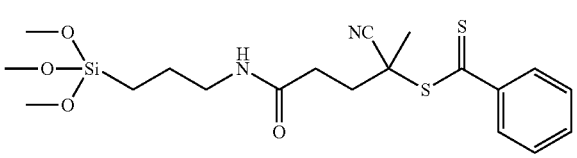

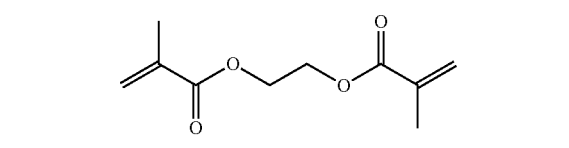
EGDMA

1

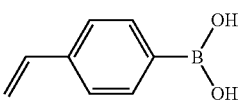

2

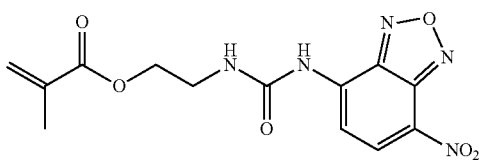

3

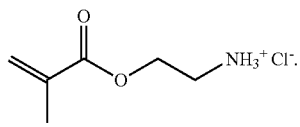

22. A molecularly imprinted polymer according to claim 1, wherein one functional monomer is 2-aminoethyl-methacrylate hydrochloride, one functional monomer is 2-(-3-(4-nitrobenzo[c][1,2,5] oxadiazo-7-yl)ureido) ethylmethacrylate and one functional monomer is 4-vinyl benzeneboronic acid.

23. A molecularly imprinted polymer according to claim 1, wherein one functional monomer is a fluorescent reporter monomer.

24. A molecularly imprinted polymer according to claim 23, wherein the functional monomer is a fluorescent reporter monomer comprising a structure selected from structures 1 and 2 depicted below

1

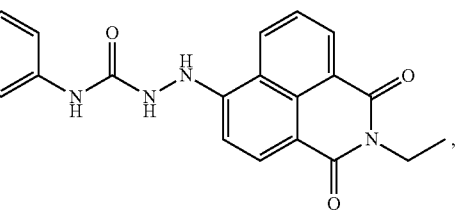

2

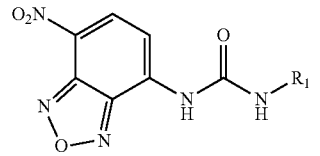

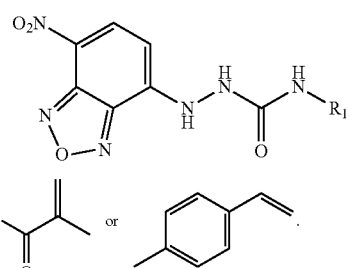

R₁: 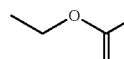 or 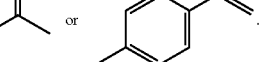

25. A molecularly imprinted polymer according to claim 23, wherein the fluorescent monomer is any of the structures shown below

2

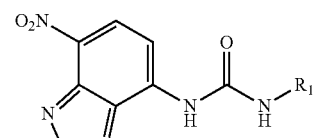

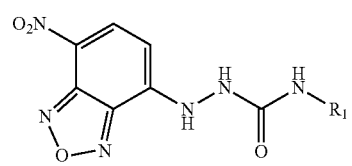

3

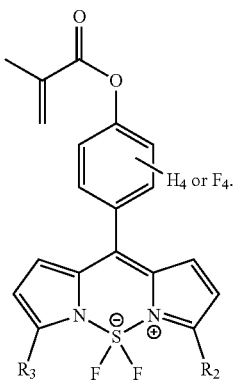

-continued

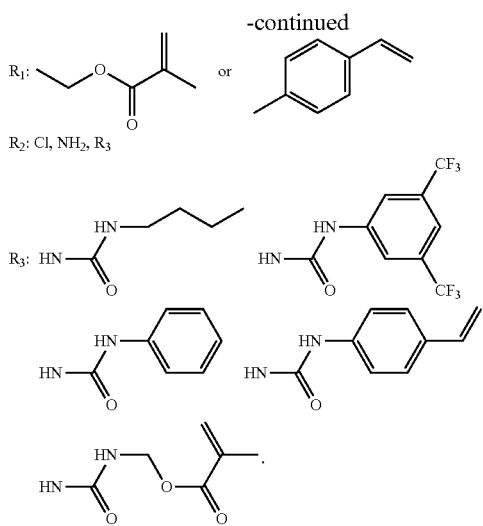

26. A molecularly imprinted polymer according to claim 1, wherein the polymer refers to a surface imprinted polymer.

27. A molecularly imprinted polymer according to claim 26, wherein the polymer is a surface imprinted polymer produced by surface initiated polymerization.

28. A molecularly imprinted polymer according to claim 26, wherein the surface imprinted polymer is prepared by any of the procedures referred to as precipitation polymerization, miniemulsion polymerization or grafting from polymerization.

29. A molecularly imprinted polymer according to claim 26, wherein the surface imprinted polymer is prepared by the technique of reversible addition fragmentation chain transfer polymerization (RAFT).

30. A molecularly imprinted polymer according to claim 26, wherein the surface imprinted polymer is prepared by the technique of reversible addition fragmentation chain transfer polymerization (RAFT) Where the RAFT groups are converted by aminolysis or radical reactions after the synthesis of the imprinted polymer.

31. A process for the preparation of a molecularly imprinted polymer, characterised in that it is obtainable by:
  a) providing a saccharide template;
  b) providing at least two functional monomers capable of cooperatively interacting with the template;
  c) providing a crosslinking monomer;
  d) polymerizing the monomers optionally dissolved in a solvent, in presence of the saccharide template; and
  e) removing the template from the formed polymer.

32. Use of the molecularly imprinted polymer according to claim 1 for in vitro;
  separations including cell separations;
  study of glycosylation status of cells;
  blood typing and cell agglutination;
  histochemical staining;
  assaying enzymes;
  sensors for molecular targets in terms of identity and concentration;
  assays (e.g. ELBA) of glycan determinants;
  flow cytometry assays;
  in vivo or in vitro biomarker imaging or as contrast agent;
  as detection tool in electrophoresis;
  as therapeutic agents (e.g. as drugs); or
  as catalysts.

33. Use of a molecularly imprinted polymer according to claim 1, in cell or tissue imaging in vitro, cell sorting in vitro, glycomics and cellular glycosylation biomarker analysis in vitro or in medicine such as in selective inhibition of cell surface interactions in vitro.

34. Use of a molecularly imprinted polymer according to claim 1; for identification and molecular characterization of circulating tumor cells (CTCS) in vitro from cancer patients.

35. A molecularly imprinted polymer according to claim 1, for use as a therapeutic through endocytosis or for intracellular targeted delivery of drugs through endocytosis of for selective inhibition of cell surface interactions.

* * * * *